US012575808B1

(12) United States Patent
Barve et al.

(10) Patent No.: US 12,575,808 B1
(45) Date of Patent: Mar. 17, 2026

(54) SYSTEMS AND METHODS FOR GUIDING ULTRASONIC PROBE POSITIONING USING SCORING-BASED CANONICAL VIEW SIMULATION MODEL

(71) Applicant: Anumana, Inc., Cambridge, MA (US)

(72) Inventors: Rakesh Barve, Bengaluru (IN);
Abhijith Chunduru, Bengaluru (IN);
Animesh Agarwal, San Mateo, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/253,831

(22) Filed: Jun. 28, 2025

(51) Int. Cl.
| | |
|---|---|
| *A61B 8/00* | (2006.01) |
| *A61B 6/03* | (2006.01) |
| *A61B 6/12* | (2006.01) |
| *A61B 8/12* | (2006.01) |
| *G06T 7/246* | (2017.01) |
| *G16H 50/20* | (2018.01) |
| *A61M 25/01* | (2006.01) |

(52) U.S. Cl.
CPC .................. *A61B 8/12* (2013.01); *A61B 6/03* (2013.01); *A61B 6/12* (2013.01); *G06T 7/251* (2017.01); *G16H 50/20* (2018.01); *A61M 2025/0166* (2013.01); *G06T 2200/24* (2013.01); *G06T 2207/10081* (2013.01); *G06T 2207/10132* (2013.01); *G06T 2207/20081* (2013.01); *G06T 2207/20084* (2013.01); *G06T 2207/30004* (2013.01)

(58) Field of Classification Search
CPC .... A61B 8/12; A61B 6/03; A61B 6/12; G06T 7/251; G06T 2200/24; G06T 2207/10081; G06T 2207/10132; G06T 2207/20081; G06T 2207/20084; G06T 2207/30004; G16H 50/20; A61M 2025/0166
See application file for complete search history.

(56) References Cited

U.S. PATENT DOCUMENTS

| | | | | |
|---|---|---|---|---|
| 10,828,106 | B2 * | 11/2020 | Schwartz | ............... G16H 50/50 |
| 12,387,365 | B1 * | 8/2025 | Barve | ....................... G06T 7/50 |
| 2022/0000448 | A1 | 1/2022 | Starns et al. | |
| 2024/0315779 | A1 | 9/2024 | PaiRaikar et al. | |

FOREIGN PATENT DOCUMENTS

| | | |
|---|---|---|
| CN | 115546287 A | 12/2022 |
| JP | 2020137974 A1 | 9/2020 |

* cited by examiner

*Primary Examiner* — Joel Lamprecht
(74) *Attorney, Agent, or Firm* — CALDWELL LLC

(57) ABSTRACT

A system for guiding ultrasonic probe positioning using scoring-based canonical view simulation model including a catheter coupled to at least a transducer, wherein the at least a transducer is configured to receive ultrasound data, a localization system configured to detect probe position data as a function of a location of the catheter, at least a processor communicatively connected to the at least a transducer and the localization system, and a memory communicatively connected to the at least a processor, and containing instructions configuring the at least a processor to receive the ultrasound data and the probe position data, generate, using a scoring-based canonical view simulation model, a movement vector as a function of the ultrasound data and the probe position data, determine, using the movement vector, real-time guidance data, and display the real-time guidance data to a user through a user interface.

18 Claims, 11 Drawing Sheets

100 ⟶

RA 508

AD 512

PA 516

RV 520

View 504

Metadata 528

ECG Display 524

500

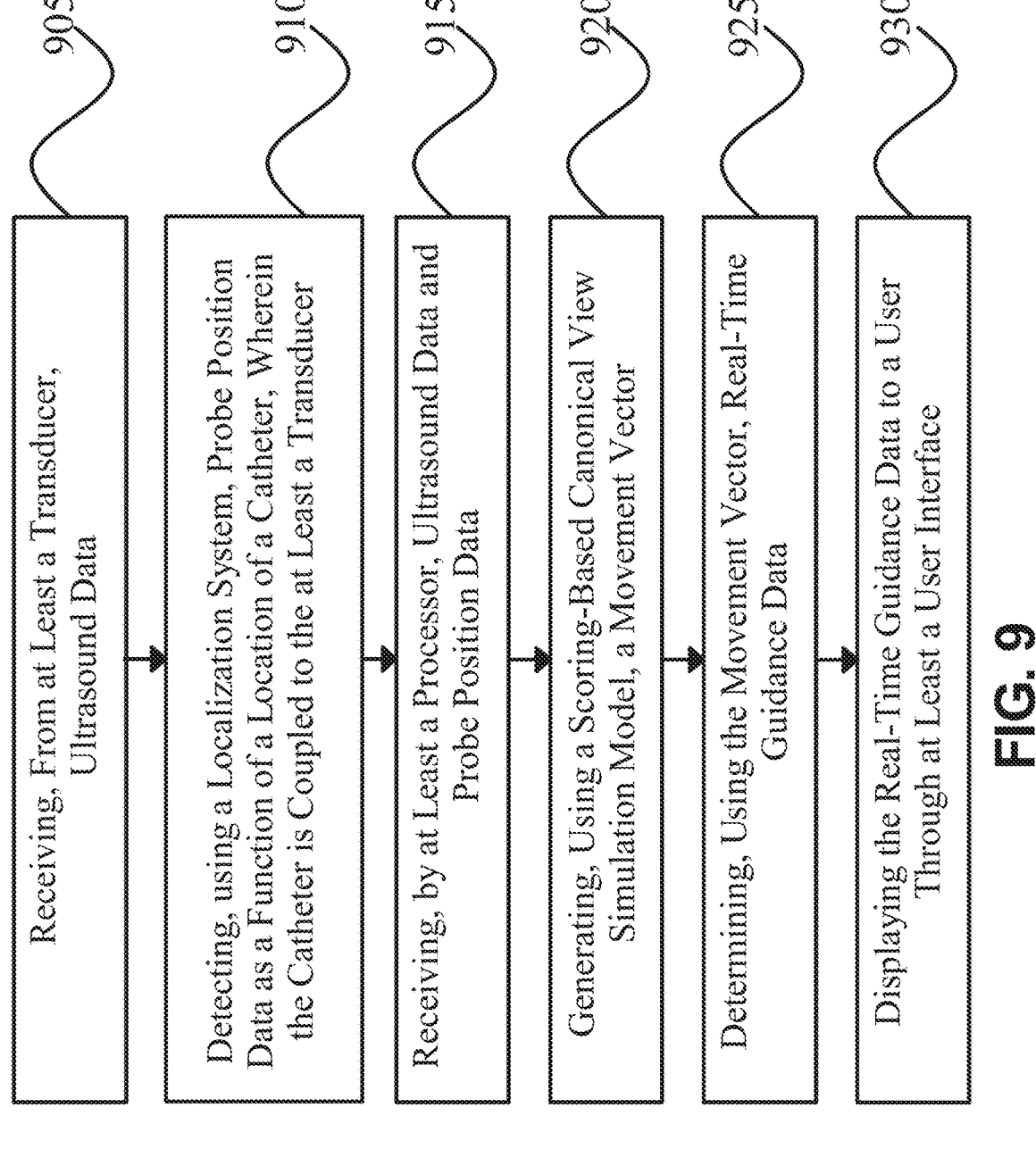

Receiving, From at Least a Transducer, Ultrasound Data — 905

Detecting, using a Localization System, Probe Position Data as a Function of a Location of a Catheter, Wherein the Catheter is Coupled to the at Least a Transducer — 910

Receiving, by at Least a Processor, Ultrasound Data and Probe Position Data — 915

Generating, Using a Scoring-Based Canonical View Simulation Model, a Movement Vector — 920

Determining, Using the Movement Vector, Real-Time Guidance Data — 925

Displaying the Real-Time Guidance Data to a User Through at Least a User Interface — 930

SYSTEMS AND METHODS FOR GUIDING ULTRASONIC PROBE POSITIONING USING SCORING-BASED CANONICAL VIEW SIMULATION MODEL

FIELD OF THE INVENTION

The present invention generally relates to the field of medical imaging modalities. In particular, the present invention is directed to systems and methods for guiding ultrasonic probe positioning using scoring-based canonical view simulation model.

BACKGROUND

Ultrasound imaging requires precise probe manipulation to obtain clinically relevant views. However, manual probe positioning is operator-dependent and can be challenging, especially for complex views such as transesophageal echocardiography (TEE). Existing methods rely on manual training and trial-and-error adjustments, leading to inefficiencies.

SUMMARY OF THE DISCLOSURE

In an aspect, a system for guiding ultrasonic probe positioning using scoring-based canonical view simulation model may include a catheter coupled to at least a transducer, wherein the at least a transducer is configured to receive ultrasound data, a localization system configured to detect probe position data as a function of a location of the catheter, at least a processor communicatively connected to the at least a transducer and the localization system, and a memory communicatively connected to the at least a processor, and containing instructions configuring the at least a processor to receive the ultrasound data from the transducer, receive the probe position data from the localization system, generate, using a scoring-based canonical view simulation model, a movement vector as a function of the ultrasound data and the probe position data, wherein the scoring-based canonical view simulation model has been trained using a reinforcement learning algorithm, determine, using the movement vector, real-time guidance data, and display the real-time guidance data to a user through a user interface.

In another aspect, a method for guiding ultrasonic probe positioning using scoring-based canonical view simulation model may include receiving, by at least a processor, ultrasound data from a transducer, receiving, by the at least a processor the probe position data from the localization system, generating, using a scoring-based canonical view simulation model, a movement vector as a function of the ultrasound data and the probe position data, wherein the scoring-based canonical view simulation model has been trained using a reinforcement learning algorithm, determining, using the movement vector, real-time guidance data, and displaying the real-time guidance data to a user through a user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein:

FIG. 9 is a flow diagram depicting an exemplary embodiment of a method for guiding ultrasonic probe positioning using scoring-based canonical view simulation model.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for guiding ultrasonic probe positioning using a scoring-based canonical view simulation model. In an embodiment, an exemplary system includes a catheter coupled to at least a transducer, a localization system for detecting probe position data, and a processor with memory configured to generate real-time guidance based on ultrasound data and probe position data using a trained scoring-based canonical view simulation model.

Aspects of the present disclosure can be used to provide real-time visual, auditory, or haptic guidance that directs optimal catheter movement during ultrasonic procedures. Aspects of the present disclosure can also be used to train a reinforcement learning model that simulates the capturing of canonical views by guiding an ultrasound device simulated from a virtual sensor positioned within computed tomography (CT) data. This is so, at least in part, because the system leverages paired ultrasound and CT data to both generate a 3D model of a target region and to train the simulation model for optimal performance.

Aspects of the present disclosure allow for improved procedural performance by displaying guidance data, such as performance metrics and visual indicators, at the user interface, thereby enabling dynamic overlay of guidance information on ultrasound images and 3D models. Exemplary embodiments illustrating aspects of the present disclosure are described below in the context of several specific examples.

Figure 1:
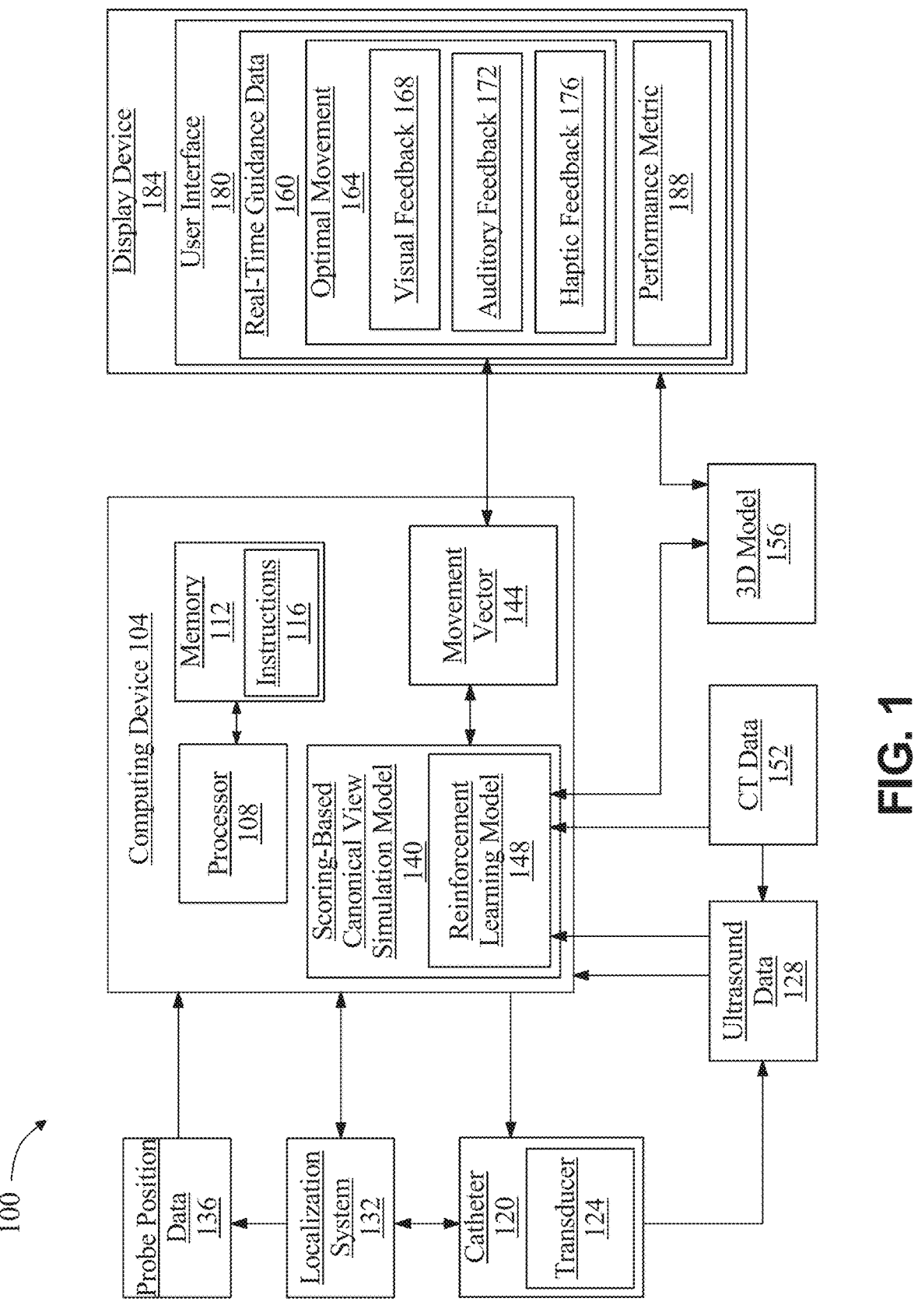
FIG. 1 is a block diagram of an exemplary embodiment of a system for guiding ultrasonic probe positioning using scoring-based canonical view simulation model.

Referring now to FIG. 1, an exemplary embodiment of a system 100 for guiding ultrasonic probe positioning using scoring-based canonical view simulation model 140 is illustrated. In an embodiment, system 100 includes a catheter 120 coupled to at least a transducer 124, wherein at least a transducer 124 is configured to receive ultrasound data 128. As used herein, a "catheter" is a thin, flexible tube used to perform medical procedures. In some embodiments, catheter 120 may be used to access the heart, blood vessels, or other organs. For instance, in cardiac procedures, catheter 120 may be designed as a cardiac catheter, optimized for navigating the vascular network around the heart to deliver therapy or capture critical imaging data. In an embodiment, catheter 120 may be constructed from biocompatible materials such as polyurethane, silicone, and/or other advanced polymers designed to navigate the body's vascular and organ systems safely. Further, catheter 120 may incorporate one or more lumens, one of which houses at least a transducer 124, while additional lumens could serve for the passage of fluids, wires, and/or other sensors. In an embodiment, catheter's 120 design might include a steerable distal tip, which may be controlled using a pull-wire or hydraulic mechanism, to enhance maneuverability through complex anatomical pathways, such as those found in cardiac or vascular procedures. Moreover, when designed as a cardiac catheter, catheter 120 may feature a soft, atraumatic tip and may be coated with lubricious materials to minimize friction and reduce the risk of vascular injury, ensuring precise imaging and therapeutic intervention during ultrasound-guided procedures.

In further reference to FIG. 1, catheter 120, as described herein, and its associated data may be consistent with one or more aspects of catheters as described in U.S. patent application Ser. No. 18/920,065, filed on Oct. 18, 2024, titled "SYSTEMS AND METHODS FOR ARTIFICIAL INTELLIGENCE ASSISTED MEDICAL DEVICE LOCALIZATION," which is incorporated by reference herein in its entirety.

Continuing to reference FIG. 1, for purposes of this disclosure, at least a "transducer" is a device that converts one form of energy into another. For example, at least a transducer 124 may take a physical input, such as sound, light, and/or pressure, and convert it into an electrical signal, or vice versa. In one embodiment, at least a transducer 124 may employ materials such as piezoelectric crystals, which generate an electrical charge when subjected to mechanical stress, making them ideal for capturing subtle variations in sound or pressure. Such piezoelectric-based ultrasound transducers may be used in diagnostic imaging, where they emit and receive high-frequency sound waves that are then converted into detailed images. In certain embodiments, at least a transducer 124 may include multiple types of transducers, which may be integrated with catheter 120 to monitor a range of physiological parameters simultaneously. For instance, a pressure transducer can detect subtle changes in blood pressure or intracavitary pressure, a temperature transducer can monitor thermal variations within tissues, an electrochemical transducer can analyze biochemical markers, and an ultrasound transducer can both emit and receive sound waves to produce real-time diagnostic images. This integration of various transducer types may enhance system's 100 ability to capture comprehensive physiological data, thereby supporting more informed clinical decision-making during medical procedures. Moreover, at least a transducer 124 containing multiple transducers can be arranged in multi-sensor arrays, allowing for simultaneous data capture from various locations or tissue depths. The integration of several transducer types within a single system may not only enhance diagnostic accuracy but also provide redundancy and cross-verification of critical physiological parameters.

In further reference to FIG. 1, "ultrasound data," as used herein refers to measured acoustic signals captured during an ultrasound procedure. An ultrasound procedure may include a "real" ultrasound procedure and/or a simulated ultrasound procedure. For example, ultrasound data 128 may include the imaging obtained from ultrasound signals, such as sound waves emitted by the probe and the echoes that return from tissues. Further, ultrasound data 128 may include imaging data, echo signal data, brightness mode image data, doppler ultrasound data, 3D/4D ultrasound data, elastography (tissue stiffness) data, motion mode data, tissue characterization and imaging parameters, quantitative measurements, time and motion data, color doppler data, power doppler data, color-enhanced ultrasound data, and/or other associated data. Additionally, and/or alternatively, ultrasound data 128 may include pseudo data, such as reconstructed 3D images, surface models, fusion data, and/or the like. In one or more embodiments, ultrasound data 128 may include TEE data, CT data 152, point-of-care ultrasound (POCUS) data, and/or the like. Further, in some embodiments, this data may mimic what would be obtained from real ultrasound scans but may include pseudo data generated from plurality of 3D imaging data.

With further reference to FIG. 1, in an embodiment, system 100 includes a localization system 132 configured to detect probe position data 136 as a function of a location of catheter 120. For purposes of this disclosure, at least a "localization system" refers to a system used to track the position and orientation of a catheter 120 within the body. In an embodiment, localization system 132 may implement one or more of: electromagnetic tracking, fluoroscopy, optical tracking, ultrasound-based localization, and/or the like. Electromagnetic tracking may use electromagnetic fields to track catheter's 120 position inside the body using sensors that may interact with an external magnetic field. Fluoroscopy, otherwise known as X-ray imaging, may be used to visualize catheter's 120 position in real-time using continuous X-ray imaging. In some cases, optical tracking may be used, which utilizes optical sensors to monitor catheter's 120 position and provide precise navigation. Further, ultrasound-based localization may include utilizing intravascular ultrasound (IVUS) to localize catheter 120 and provide detailed images of the coronary arteries and/or heart chambers, allowing for better guidance during a procedure.

In further reference to FIG. 1, in an embodiment, localization system 132, as described herein, and its associated data may be consistent with one or more aspects of the systems and methods of localization as described in U.S. patent application Ser. No. 19/188,942, filed on Apr. 24, 2025, titled "APPARATUS AND METHOD FOR CONTROLLING A ROBOTIC FRAMEWORK TO PERFORM IMAGING MODALITIES," as further described in U.S. patent application Ser. No. 18/920,065, filed on Oct. 18, 2024, titled "SYSTEMS AND METHODS FOR ARTIFICIAL INTELLIGENCE ASSISTED MEDICAL DEVICE LOCALIZATION," and as further described in U.S. patent application Ser. No. 18/764,853, filed on Jul. 5, 2024, titled "SSYSTEM AND METHOD FOR LOCATING A MEDI- CAL DEVICE USING AN ELECTRICAL FIELD CRE-
ATION," each of which is incorporated by reference herein
in their entirety.

With continued reference to FIG. 1, In an embodiment,
localization system 132 may include an ultrasound-based
localization system. As used in this disclosure, an "ultra-
sound-based localization system" is a method used to deter-
mine the position and movement of objects within the body
by employing high-frequency sound waves. The ultrasound-
based localization system may involve the use of an ultra-
sound transducer that emits sound waves, which then reflect
off internal structures and are captured by transducer or other
sensors. Continuing, the reflected sound waves may be
processed to create real-time images or data points that
represent the location and motion of the tracked object, such
as catheter 120 or other medical instruments. The ultra-
sound-based localization system may be particularly useful
in medical procedures because it provides real-time, non-
invasive visualization of internal body structures. The ultra-
sound-based localization system may allow clinicians to
guide instruments accurately within the body, enhancing the
precision and safety of procedures like catheter ablation,
biopsies, or other interventions. This technology may be
integrated with other systems to provide comprehensive
spatial and functional mapping of the area being treated. For
example, localization system 132 may utilize ultrasound
technology, where an array of ultrasound transducers are
positioned around the patient. Catheter 120 may be fitted
with miniature ultrasound receivers, which may detect emit-
ted ultrasound waves. Localization system 132 may calcu-
late catheter 120 position based on the time it takes for the
ultrasound waves to reach the receivers, allowing for precise
localization of catheter's 120 tip during a procedure.

In continued reference to FIG. 1, "probe position data," as
used herein, refers to the spatial information about an
ultrasound probe's location and orientation. For example,
probe position data 136 may include, without limitation,
spatial coordinates, orientation and angle, probe position in
relation to the body, tracking data, probe depth and pressure,
probe type and configuration, ultrasound beam direction,
tracking system integration data, calibration information,
temporal data, probe velocity, and/or other associated data.
In an embodiment, probe position data 136 may record the
ultrasound probe's movements, angles, and/or the depth of
the scanning field, ensuring accurate representation of how
different probe positions may affect the ultrasound image.
This data may allow for dynamic visualizations and inter-
actions during an ultrasound procedure.

In further reference to FIG. 1, in a non-limiting example,
probe position data 136 may be derived from ultrasonic
feedback, where localization system 132 uses an array of
transducers to emit ultrasonic waves and detect their reflec-
tions from catheter 120. The resulting probe position data
136 may indicate the spatial coordinates of catheter 120
within the body and/or a simulated body and can be pro-
cessed to adjust its positioning dynamically. In a non-
limiting example, probe position data 136 may be repre-
sented as Cartesian coordinates (x, y, z) that define the
location of catheter 120 within a three-dimensional (3D)
space. For instance, localization system 132 may generate
position signals, for example, (12.5, 8.3, 4.7), indicating the
exact spatial position of catheter 120 relative to a defined
origin point. Continuing, these coordinates may be continu-
ously updated in real time to reflect the movement of
catheter 120, allowing precise tracking and guidance during
a medical procedure. In another non-limiting example, probe
position data 136 may include additional data such as orientation or angular displacement. For instance, probe
position data 136 may take the form of a six-dimensional
representation (x, y, z, roll, pitch, yaw), where the first three
dimensions define the location and the latter three define the
orientation of catheter 120. Continuing, this may enable
localization system 132 to provide more detailed guidance,
particularly for tasks requiring precise alignment, such as
positioning an ultrasonic transducer at a specific angle
relative to a target region. In another non-limiting example,
probe position data 136 may be expressed as polar coordi-
nates (r, θ, φ), where "r" represents the radial distance from
a reference point, "θ" the azimuthal angle, and "φ" the polar
angle. Such a representation may be particularly useful in
applications involving circular or spherical navigation paths,
such as guiding catheter 120 around the walls of a heart
chamber or within a curved blood vessel. Continuing, probe
position data 136 may be converted into actionable move-
ment instructions for a user to control the positioning and
orientation of catheter 120 effectively.

In further reference to FIG. 1, in an embodiment, probe
position data 136 may include a position, orientation, and
velocity of an ultrasound probe in relation to at least a 3D
model 156 and one or more movements of the ultrasound
probe in relation to at least a 3D model 156. In an embodi-
ment, probe position data 136 may capture both static and/or
dynamic information. For example, position may include the
spatial coordinates of the ultrasound probe at a given
moment in time, indicating its location relative to a target 3D
model 156. This may aid in mapping the exact placement of
the probe relative to a patient and/or a specific region of
interest within the 3D model 156. Orientation may include
the angular position and/or rotation of the ultrasound probe,
in some cases, orientation may be represented as a set of
angles and/or rotation matrix that describes the ultrasound
probe's angle relative to a reference plane, such as the
anatomical position of a patient and/or a 3D model 156. The
orientation may ensure that the ultrasound probe is aligned
correctly for imaging from the appropriate angle. One or
more movements may include data describing the continu-
ous and/or discrete movements of an ultrasound probe over
time in relation to a 3D model 156. For example, this may
include the trajectory and/or path taken by the ultrasound
probe, as well as changes in orientation as a user manipu-
lates the ultrasound probe. Further, one or more movements
may help track how the ultrasound probe is swept across the
model and/or how it rotates. Alternatively, one or more
movements may be related to enhancing imaging data or
capturing a canonical view precisely. In an embodiment, the
ultrasound probe position data 136 may be tied to one or
more 3D models 156 representing the anatomy or organs of
interest. The 3D models 156 may include models derived
from a plurality of 3D imaging data, which may, in some
cases, include 3D models 156 constructed from 2D images/
scans.

In continued reference to FIG. 1, system 100 includes a
computing device 104. Computing device 104 includes at
least a processor 108 communicatively connected to a
memory 112, wherein memory 112 contains instructions 116
configuring at least a processor 108 to initiate one or more
methods or tasks as described herein. Further, at least a
processor 108 may be communicatively connected to at least
a transducer 124. As used in this disclosure, "communica-
tively connected" means connected by way of a connection,
attachment or linkage between two or more relata which
allows for reception and/or transmittance of information
therebetween. For example, and without limitation, this
connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

In further reference to FIG. 1, in an embodiment, at least a processor 108 is configured to receive ultrasound data 128 and probe position data 136. At least a processor 108 may interface with the ultrasound transducer to capture real-time imaging data, while simultaneously acquiring probe position data 136 from a localization system 132 that tracks the catheter's 120 spatial orientation. This data fusion may enable at least a processor 108 to correlate anatomical imaging with precise spatial positioning, facilitating enhanced visualization and guidance during procedures. Furthermore, at least a processor 108 may execute algorithms that integrate and analyze these data streams to generate actionable feedback, optimize imaging parameters, and support decision-making in real time.

With continued reference to FIG. 1, in an embodiment, ultrasound data 128 and probe position data 136 may include live data. Further, ultrasound data 128 and probe position data 136 may be received from a real ultrasonic procedure. For purposes of this disclosure, "live data" refers to information obtained from actual procedures performed on live subjects. For example, data captured during a real ultrasonic procedure. In contrast, "simulated data," as used herein, is artificially generated using computational models or algorithms rather than being derived from real-world observations. In an embodiment, ultrasound data 128 and probe position data 136 may include simulated data obtained from a simulated ultrasound, enabling the system to be used for technician training prior to performing procedures on patients. For purposes of this disclosure, an "ultrasonic procedure" refers to a medical diagnostic or therapeutic technique that employs high-frequency sound waves to visualize internal structures, assess organ function, or guide treatment within the body. In diagnostic applications, an ultrasound probe may emit sound waves that penetrate the body, with the returning echoes recorded and translated into images to detect abnormalities such as tumors, cysts, or blood flow irregularities. In therapeutic applications, ultrasound can guide procedures like biopsies, by accurately locating the area for sample collection, or facilitating treatments such as lithotripsy, where focused sound waves are used to fragment kidney stones. In an embodiment, ultrasonic images may be received from an ultrasonic procedure device, with the procedure generating such images for clinical evaluation or intervention.

In further reference to FIG. 1, in an embodiment, ultrasound data 128 and probe position data 136 may be obtained using an ultrasonic imaging device. As used herein, an "ultrasonic imaging device" is a device configured to collect ultrasonic images. Further, in an embodiment, ultrasound data 128 may include a plurality of ultrasonic images. As used herein, an "ultrasonic image" is an image generated as a function of a reflection of a sound wave off a structure. Non-limiting examples of ultrasonic images and/or imaging techniques may include intracardiac echo (ICE) images, transthoracic echocardiograms (TTE), transesophageal echocardiograms (TEE), and point of care ultrasound (PO-CUS). In some embodiments, the plurality of ultrasonic images may include a TEE image. In some embodiments, a TEE image may include a 2D TEE. In some embodiments, a TEE image may include a 3D TEE. In some embodiments, plurality of ultrasonic images may include an ICE image. In some embodiments, a set of ultrasonic images of the patient's organ may include an image selected from the list consisting of a transesophageal echocardiogram image, a transthoracic echocardiogram image, and a point-of-care ultrasound image. An ultrasonic image of plurality of ultrasonic images may depict an organ and/or tissue of a subject. An ultrasonic image of plurality of ultrasonic images may depict a heart, lung, spleen, liver, kidney, muscle, skeleton, intestine, stomach, vein, and/or artery. In some embodiments, an ultrasonic image may depict a heart, and/or a left atrium, left atrial appendage, left ventricle, right ventricle, and/or a right atrium of a heart.

Still referring to FIG. 1, in some embodiments, an ultrasonic image may include transesophageal echocardiogram (TEE) image. In some embodiments, a TEE image may include a view of an ostial diameter and/or length. In some embodiments, the plurality of ultrasonic images may include ultrasonic images captured at the same position, and different orientations with respect to a subject's heart. In some embodiments, a TEE image may include a view of an ostial diameter and/or length from one or more angles on a mid-esophageal view. As examples, a TEE image may include a view of a subject's heart and/or an ostial diameter and/or length from 1, 2, 3, 4, 5, 6, 7, 8, 9, or 10 different angles on a mid-esophageal view. In a non-limiting example, a TEE image may include a view of a subject's heart and/or an ostial diameter and/or length from 4 different angles (0°, 45°, 90°,) 135° on a mid-esophageal view. In some embodiments, angles of images may describe a rotational position of an ultrasound transducer relative to a subject's heart. In additional non-limiting examples, a TEE image may include a view of a subject's heart and/or an ostial diameter and/or length from 0° (which may provide a four chamber view), 45-60° (which may provide a two chamber view and in some embodiments may be used to identify a thrombus), 90° (which may provide a long-axis view), 120-135° (which may provide a long-axis view of a left atrial appendage) and/or 135-160° (which may provide an aortic valve long axis view) on a mid-esophageal view. In some embodiments, an ostial diameter and/or length includes an ostial diameter and/or length of a left atrial appendage (LAA) of a heart and/or another location at which a cardiac implant may be placed. In some embodiments, TEE images may include a view of an ostial diameter and/or length from 4 different angles, such as, as a non-limiting example, 0°, 45°, 90°, and 135°.

Still referring to FIG. 1, in some embodiments, plurality of ultrasonic images may include an intracardiac echocardiography (ICE) image. As used herein, an "ICE image" is an ultrasound image obtained from within the heart's chambers or blood vessels. In some cases, ICE images may be captured using a specialized catheter equipped with an ultrasound transducer that is inserted into the body and guided to the heart of subject. In an embodiment, an ultrasound image may provide a detailed and real-time visualization of cardiac anatomy. ICE images may also include internal structures, functions, and blood flow patterns of the heart of a subject. Plurality of ultrasonic images may be related in terms of content, time of capture, sequence, or any other relevant parameters described herein. In a non-limiting example, each image of plurality of ultrasonic images may represent a particular view, angle, or perspective of an object, subject, or scene, and may be in two-dimensional (2D) or 3D format. Images of plurality of ultrasonic images may include, without limitation, any two-dimensional or three-dimensional images of any anatomy or anatomical structure, including without limitation images of any internal organ, tissue including muscular, connective tissue, epithelial tissue, and/or nervous tissue, bone, and/or any other element that may be imaged within a human and/or animal body.

Still referring to FIG. 1, in a non-limiting example, plurality of ultrasonic images may illustrate structures of a heart of a subject which may include chambers (e.g., four chambers including left and right atria and left and right ventricles), valves (i.e., the structures that regulate blood flow between chambers and vessels, including mitral, tricuspid, aortic, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), LAA and other appendages, pathological features (e.g., any abnormalities, defects, and/or the like), and/or other components of a heart.

Still referring to FIG. 1, in an embodiment, each ultrasonic image of plurality of ultrasonic images may include a particular view of subject's heart chambers, valves, vessels, and/or the like. In a non-limiting example, plurality of ultrasonic images may include multiple views e.g., different angles and perspectives of a subject's heart. In another embodiment, plurality of ultrasonic images may be arranged in a temporal sequence. In a non-limiting example, plurality of ultrasonic images may include a series of images captured over time, allowing for an observation of dynamic cardiac functions such as beating, blood flow, and/or the like. In some cases, each ultrasonic image of plurality of ultrasonic images may include a corresponding timestamp, wherein the timestamp may include an indicator showing a date and time of when the corresponding ultrasonic image was taken.

Still referring to FIG. 1, in an embodiment, at least a processor 108 is configured to generate, using a scoring-based canonical view simulation model 140, a movement vector 144 as a function of ultrasound data 128 and probe position data 136. For purposes of this disclosure, "canonical view" is a standardized representation of an anatomical structure in an imaging modality. A canonical view may be defined by specific anatomical landmarks and optimal imaging angles, ensuring that key diagnostic features are consistently and clearly visualized. By providing a uniform perspective, canonical views may facilitate accurate diagnosis, comparison over time, and effective guidance during medical procedures. A "scoring-based canonical view simulation model," as used throughout this disclosure, is a computational framework that evaluates various simulated imaging configurations by assigning scores that reflect the quality or diagnostic value of each simulated view. Scoring-based canonical view simulation model 140 may be trained on datasets containing ultrasound data 128, probe position data 136, and ideal imaging outcomes, enabling it to learn the characteristics of optimal canonical views. During operation, scoring-based canonical view simulation model 140 may use these scores to predict and recommend the best probe positions or imaging parameters to capture superior views, thereby guiding the ultrasound device toward the most diagnostically useful configuration. This approach may leverage techniques such as reinforcement learning to continuously improve its predictions and provide real-time procedural guidance.

In further reference to FIG. 1, for purposes of this disclosure, a "movement vector" is a mathematical representation that describes a projected or suggested change in position or orientation of an object or point in space. In some cases, this may include the change in position of an object or point in space over a given period of time. For example, a change in position or orientation of catheter 120. In an embodiment, movement vector 144 may include both direction and magnitude. Wherein, movement vector 144 points in the direction of movement, and the length of the vector represents the distance the object has moved, or the magnitude of the movement. In a 2D space, movement vector 144 may be represented with (x, y) coordinates. Whereas in 3D space movement vector 144 may be represented with (x, y, z) coordinates. In an embodiment, at least a processor 108 may generate movement vector 144 as a function of ultrasound data 128 and probe position data 136 by comparing ultrasound data 128 and probe position data 136 at a first time and ultrasound data 128 and probe position data 136 at a second time. For example, if ultrasound data 128 and probe position data 136 indicate that catheter 120 has moved from position A (1, 2) to position B (4, 6) movement vector 144 would be v=(4-1, 6-2)=(3, 4). This may indicate that catheter 120 moved 3 units in the x-direction and 4 units in the y-direction.

With continued reference to FIG. 1, in an embodiment, system 100 may be equipped with a natural language processing (NLP) module integrated within its processing unit, enabling it to receive natural-language commands from a user. The NLP module may interpret commands such as "move the catheter 120 slightly to the left" or "rotate the probe for a clearer view," extracting the intent and relevant parameters necessary to provide guidance on how the user should adjust the device's positioning. In some cases, the NLP module may interpret commands related to specific canonical views. For example, "Show me the apical four-chamber view" or "Adjust the probe for a parasternal long-axis view." Commands might also specify adjustments like "Rotate the probe to capture an ideal subcostal view" or "Shift slightly to the left for a better view of the mitral valve. The NLP module may translate these verbal instructions into actionable directives by mapping them onto predefined movement commands, which are then converted into movement vectors 144 by system's 100 scoring-based canonical view simulation model 140. These movement vectors 144 may represent quantifiable recommendations, specifying precise adjustments in position, orientation, or both, that inform the user how to reposition the ultrasound device to capture the optimal canonical view as defined by scoring-based canonical view simulation model 140. In an embodiment, system 100 may leverage its training on historical ultrasound and CT data 152 pairs to determine the most effective vector for achieving the desired imaging outcome. By transforming natural-language commands into quantifiable movement vectors 144, system 100 provides clinicians with an intuitive and interactive means of receiving real-time guidance on device positioning, thereby enhancing procedural efficiency and diagnostic accuracy. In some cases, system 100 may be integrated with automated robotic system that may make adjustments based on these verbal commands.

In continued reference to FIG. 1, in training scenarios, an embodiment incorporating the NLP module may enhance a user's learning experience by enabling expert instructors, whether remote or local to provide real-time guidance through natural language commands. For instance, an expert may verbally instruct a trainee, and ultimately system 100, with commands such as, "Adjust the probe for a parasternal long-axis view," or "Rotate slightly to capture the apical four-chamber view." System 100 may then interpret these commands and overlay the corresponding movement vectors 144 and visual guidance onto the trainee's display, enabling them to see exactly how to reposition catheter 120 for optimal imaging. Further, in testing situations, an instructor's indicated view may be received by both the trainee and system 100. System 100 may however, not display real-time guidance, but track, using scoring-based canonical view simulation model 140 movements of the trainee, generating a performance metric. This may ensure that the trainees' movements are objectively evaluated. This interactive feedback mechanism not only accelerates the acquisition of proper procedural techniques but may also bridge the gap between theoretical instruction and practical application, fostering a more engaging and effective training environment.

With further reference to FIG. 1, in an embodiment, an NLP module, as described herein, may be consistent with one or more aspects of the voice recognition module as described in U.S. patent application Ser. No. 19/253,825, filed on Jun. 28, 2025, titled "VOICE-CONTROLLED ULTRASONIC IMAGING AND METHODS THEREOF," which is incorporated by reference herein in its entirety.

In further reference to FIG. 1, in an embodiment, at least a processor 108 may be further configured to train scoring-based canonical view simulation model 140, wherein training includes using a plurality of ultrasound and CT data 152 pairs to simulate a capturing of canonical views by guiding an ultrasound device that is simulated from a virtual sensor positioning in CT data 152. The training may involve simulating a procedure of capturing canonical views by guiding an ultrasound device that is modeled as a virtual sensor positioned within the CT data 152, thereby replicating the conditions of an actual ultrasound procedure. The scoring-based approach may assign quantitative values to simulated views based on their alignment with predefined criteria for diagnostic quality, such as clarity, anatomical coverage, and the visibility of key landmarks. By iteratively adjusting the simulation parameters through techniques such as reinforcement or supervised learning, at least a processor 108 may refine scoring-based canonical view simulation model 140 to accurately predict the optimal probe positioning and imaging configurations needed to achieve high-quality canonical views during real-time procedures.

In continued reference to FIG. 1, in an embodiment, scoring-based canonical view simulation model 140 may include a reinforcement learning model 148 trained using computed tomography (CT) data. For purposes of this disclosure, "CT data," refers to the information generated by a CT scan. For example, CT data 152 may include, without limitation, sequential axial image slices of a patient's head, chest, or abdomen captured during a CT scan. These slices can be further processed into volumetric datasets that allow for three-dimensional reconstructions of anatomical structures. Additionally, CT data 152 may include DICOM files containing metadata such as radiodensity values and patient positioning, as well as segmented images where specific organs or lesions are highlighted for diagnostic or therapeutic planning. A "CT scan," as used herein is a medical imaging technique that uses X-rays and computer processing to create detailed cross-sectional images of the body.

With further reference to FIG. 1, a "reinforcement learning model," as used throughout this disclosure, is a machine-learning model where an agent learns to make decisions by interacting with an environment in order to maximize some notion of cumulative reward over time. The agent may take actions, receive feedback in the form of rewards and/or penalties, and adjust its behavior over time to maximize cumulative rewards. Key components of reinforcement learning may include the agent, environment, state, action, reward, policy, and/or value function. In reinforcement learning, an "agent," is the decision-maker that preforms actions in the environment. The "environment," as used herein, refers to the system with which the agent interacts. A "state," as used herein, is a representation of the environment at a given time.

"Action," as used herein, refers to the choices the agent can make to affect the environment. As used herein, "reward" refers to the feedback the agent receives after taking an action, indicating how good or how bad that action was. A "policy," as used herein, is a strategy or mapping from states to actions that the agent follows to decide what actions to take. As used herein, a "value function" is a measure of the long-term reward an agent can expect from a given state, guiding the agent's decision making. In an embodiment, a reinforcement learning (RL) model may aim to find an optimal policy that maximizes the total expected reward over time, in some cases using techniques such as Q-learning, deep Q networks (DQN), and/or policy gradient methods.

In further reference to FIG. 1, in an embodiment, the RL agent may include the scoring-based canonical view simulation model 140. The environment may include CT data 152 and/or 3D anatomical data. The state may be represented by the position of catheter 120 at any given point in the procedure, as well as surrounding tissue structures derived from probe position data 136 and 3D models 156. The actions may include potential movements and/or changes in catheter's 120 orientation and position. RL model may decide on the best action, such as direction, angle, and/or path, to achieve an optimal canonical view based on the current state. The reward may include a signal given to the agent based on the success of its action. The reward may include a signal provided to the agent based on the success of its action. For example, a positive reward may be given for actions that position catheter 120 in a manner that yields a thorough and diagnostically useful canonical view while avoiding obstacles, whereas negative rewards may be assigned when catheter 120 deviates from parameters that produce an optimal canonical view or come too close to obstacles. The policy may include the strategy that the RL agent learns to determine the best sequence of actions to capture optimal canonical views. For purposes of this disclosure, the "optimal sequence" is defined as the policy that maximizes the cumulative reward, leading to the most successful acquisition of canonical views in the fewest steps. During training, scoring-based canonical view simulation model 140 may interact with the environment and, over time, learn through trial and error which actions result in successful capture of canonical views. Furthermore, scoring-based canonical view simulation model 140 may use training data, including CT data 152, 3D imaging, probe position data 136, and 3D models 156, to identify patterns and optimize its guidance for achieving optimal canonical views, potentially taking into account the number of views needed to produce an accurate representation of the target region.

Still referring to FIG. 1, at least a processor 108 may be configured to compute, using a reward function, visibility scores for a canonical view of a plurality of canonical views of ultrasound data 128 as a function of segmented ultrasound data and simulated probe position data. As used in this disclosure, "reward function" is a function that assigns a numerical value to an outcome based on predefined performance criteria. In an embodiment, the numerical value is the reward. Without limitation, the reward function may evaluate the quality, accuracy, and/or visibility of cardiac structures in an ultrasound image and provide feedback to guide optimization processes, such as reinforcement learning algorithms and/or image enhancement models. Without limitation, the reward function may be designed to maximize the clarity of key anatomical features while minimizing distortions or irrelevant data. As used in this disclosure, a "visibility score" is a quantitative measure representing the presence of a target region of interest within an image. In an embodiment, the visibility score may be computed based on factors such as contrast, segmentation accuracy, structural completeness, and/or similarity to a reference image. Without limitation, a higher visibility score may indicate a well-aligned view of the target region of interest, such as the cardiac structure, while a lower visibility score may suggest occlusions, artifacts, and/or misalignment of the canonical view and a predefined canonical ultrasound view.

With continued reference to FIG. 1, as used in this disclosure, "canonical views" are a set of standardized or predefined optimal viewing perspectives of a structure in an imaging system. Without limitation, the canonical views may be determined based on medical best practices, expert-labeled datasets, predefined imaging protocols, and the like. In an embodiment, the canonical views may serve as reference positions to ensure consistency in image acquisition, diagnosis, or procedural guidance. Simulated probe position data may be used to model different probe placements and angles, allowing the system to evaluate and optimize imaging perspectives without requiring direct physical probe manipulation. Alternatively, simulated probe position data may mirror probe position data 136 of a live medical procedure. The simulated probe position data may be derived from historical scan data, reinforcement learning models, predefined anatomical positioning guidelines, and the like.

With continued reference to FIG. 1, the reward function may include scoring-based canonical view simulation model 140, wherein scoring-based canonical view simulation model 140 is trained using one or more reinforcement learning techniques based on historical scores corresponding to historical canonical views. Scoring-based canonical view simulation model 140 may be trained using reinforcement learning techniques to optimize imaging parameters, probe positioning, or visibility scores based on historical data. The reward model may refine its predictions over time by learning from past successes and failures in achieving optimal anatomical visualization. As used in this disclosure, "reinforcement learning techniques" are machine learning methods that involve training an agent to take actions in an environment to maximize cumulative rewards over time. In an embodiment, the reinforcement learning techniques may rely on an iterative process of exploration and exploitation, where scoring-based canonical view simulation model 140 may learn from past actions and the corresponding rewards. As used in this disclosure, "historical scores" refer to previously recorded numerical evaluations assigned to past imaging attempts based on visibility, alignment, or segmentation quality. The historical scores may be used to train scoring-based canonical view simulation model 140, enabling system 100 to predict optimal imaging conditions and positions based on prior data. As used in this disclosure, "historical canonical views" are previously captured imaging perspectives that serve as reference points. In an embodiment, the historical canonical views may help evaluate new image acquisitions. The historical canonical views may be manually selected by experts or automatically identified by machine-learning algorithms as ideal representations of a given cardiac structure.

With continued reference to FIG. 1, in a non-limiting example, the training of scoring-based canonical view simulation model 140 may be consistent with one or more aspects of the model as described in U.S. patent application Ser. No. 19/253,817, filed on DATE Jun. 28, 2025, titled "APPARATUS AND METHOD FOR GENERATNG AN OPTIMAL PROBE POSITION AS A FUNCTION OF AT LEAST A VISIBILITY SCORE FOR A PLURALITY OF CANONICAL VIEWS," which is incorporated by reference herein in its entirety.

With further reference to FIG. 1, in an embodiment, at least a processor 108 may be further configured to receive a 3D model 156 of a target region, wherein the 3D model 156 is generated using CT data 152. In some cases, at least a processor 108 may receive a 3D model 156 from a 3D model 156 generator. Alternatively, at least a processor 108 may be configured to generate a 3D model 156 of a target region using ultrasound data 128. A "3D model," as used throughout this disclosure, is a digital representation of an object or structure in three-dimensional space. 3D models 156 may include, without limitation, vertices, edges and faces, meshes, textures and materials, rendering, animation and rigging, and/or the like. For purposes of this disclosure, a "target region" refers to a specific area or location that is the focus of interest or action in a particular context. In an embodiment, the target region may be related to a system and/or specific organ, such as a heart. For example, the target region may be specific to the ultrasonic procedure being undergone. In a non-limiting embodiment, 3D model 156 generator may generate 3D models 156 as described above in reference to generating 3D models 156, which may include any incorporations by reference.

With continued reference to FIG. 1, at least a processor 108 may be configured to receive a plurality of 3D imaging data and generate, using the plurality of 3D imaging data, simulated data comprising segmented ultrasound data. As used in this disclosure, "3D imaging data" is a dataset comprising volumetric image information captured from a three-dimensional imaging modality. In an embodiment, the 3D imaging data may be acquired from medical imaging systems such as ultrasound, computed tomography (CT), magnetic resonance imaging (MRI), optical coherence tomography (OCT), and the like. Without limitation, the 3D imaging data may include spatially indexed pixel or voxel representations, allowing for depth perception, cross-sectional visualization, and reconstruction of cardiac structures in three dimensions. As used in this disclosure, "segmented ultrasound data" is ultrasound imaging data that has been processed to distinguish and isolate specific regions of interest. As used in this disclosure, "regions of interest" are areas within an ultrasound image that have been identified and isolated for further analysis, measurement, or visualization. In an embodiment, the regions of interest may correspond to cardiac structures, pathological features, or other clinically relevant areas that are distinguished from surrounding tissue based on predefined criteria such as intensity, texture, shape, or contrast. Regions of interest may be determined using manual selection, automated image processing algorithms, or artificial intelligence-based segmentation techniques. Without limitation, the process of segmentation may involve applying image processing techniques such as thresholding, edge detection, artificial intelligence-based classification, and the like, to enhance visualization and analysis. The segmented ultrasound data may be used to identify abnormalities, guide medical procedures, or improve diagnostic accuracy. Without limitation, at least a processor 108 may process the plurality of 3D imaging data using computational techniques, such as image registration, filtering, and segmentation algorithms, to extract and generate simulated data. Continuing, the simulated data may include segmented ultrasound data, where specific cardiac structures or regions of interest have been isolated or highlighted. In a non-limiting example, system 100 may enhance visualization for diagnostic, therapeutic, procedural guidance applications, and the like by segmenting the ultrasound data.

With continued reference to FIG. 1, the plurality of 3D imaging data may include CT data 152. In an embodiment, CT data 152 may include of a series of two-dimensional (2D) image slices that, when reconstructed, form a three-dimensional (3D) representation of internal structures. In an embodiment, CT data 152 may include intensity values corresponding to different tissue densities, enabling detailed visualization of anatomical features. In an embodiment, CT data 152 may be processed for diagnostic evaluation, segmentation, 3D modeling applications, and the like. Without limitation, the plurality of 3D imaging data may include CT data 152, which consists of volumetric image datasets generated from CT scans. In an embodiment, the CT data 152 may be composed of multiple two-dimensional cross-sectional image slices that, when processed, form a three-dimensional representation of internal structures, such as a patient's heart. Without limitation, the CT data 152 may provide high-resolution imaging of anatomical features, allowing for detailed visualization, segmentation, and diagnostic analysis. At least a processor 108 may utilize the CT data 152, along with other imaging modalities, to generate simulated data and/or enhance the accuracy of segmented ultrasound data.

With continued reference to FIG. 1, system 100 may further include a data simulator configured to generate the simulated data, wherein the data simulator may include a machine-learning model trained on simulation training dataset, the simulation training dataset including historical image data associated with historical position data. As used in this disclosure, "data simulator" is a system designed to generate synthetic data that mimics real-world imaging. In an embodiment, the data simulator may process input data, such as medical imaging datasets, computational models, and/or sensor readings, to create simulated representations for analysis, training, validation, system testing, and the like. The data simulator may incorporate machine-learning algorithms, mathematical modeling, physics-based rendering, and the like, to replicate expected outputs under various conditions. As used in this disclosure, "simulation training dataset" is a collection of data used to train a machine-learning model for generating simulated data. The simulation training dataset may include live or synthetic data samples, labeled or annotated for supervised learning, unsupervised learning, or reinforcement learning tasks. Without limitation, the simulation training dataset may consist of historical image data, position data, sensor readings, feedback data, and/or other relevant parameters to enhance model accuracy and predictive performance. As used in this disclosure, "historical image data" is a set of previously acquired imaging data that serves as a reference for training. The historical image data may include medical images, diagnostic scans, previously generated simulated imaging data, and/or other visual datasets collected over time from the same or different subjects. Historical image data may be utilized to improve machine-learning model, detect trends, refine simulated imaging outputs, and the like. As used in this disclosure, "historical position data" is a dataset containing previously recorded positional information associated with an ultrasound probe. In an embodiment, the historical position data may include spatial coordinates, motion trajectories, orientation angles, and/or alignment references, which may be used for tracking, training predictive models, or enhancing imaging simulations. In an embodiment, the training simulator dataset may include historical image data associated with historical position data, allowing the machine-learning model to learn patterns and relationships between image characteristics and spatial positioning of the ultrasound probe. The trained model may then generate simulated image outputs that replicate expected imaging results based on input conditions. Continuing, this capability may improve the data simulator by facilitating training of simulated data generation.

With continued reference to FIG. 1, in a non-limiting example, the simulated data may be consistent with one or more aspects of the simulated data, simulated environment, and the like, as described in U.S. patent application Ser. No. 19/188,841, filed on DATE Jun. 28, 2025, titled "SYSTEM AND METHOD FOR SWEEP TRAJECTORY SIMULATION," which is incorporated by reference herein in its entirety.

With continued reference to FIG. 1, the data simulator may further be configured to generate simulated ultrasound data of the simulated data, wherein the data simulator may include a generative adversarial network that has been trained on the simulation training dataset, the simulation training dataset may further include a plurality of real-images and a plurality of simulated images. In an embodiment, generating simulated data may include using one or more machine-learning algorithms to generate simulated ultrasound images. By training one large dataset, machine-learning algorithms may create synthetic images based on a given input, such as probe position, tissue type, and/or pathology. For example, without limitation, a generative adversarial network (GAN) may be used to generate simulated data. In an embodiment, a GAN may include both a generator and a discriminator. The generator may include a neural network designed to produce synthetic ultrasound data, such as images. Given certain inputs such as probe position, tissue type, and/or pathology, the generator may learn to create realistic ultrasound images that mimic the appearance of real ultrasound scans. In an embodiment, the generator may use training data, such as real ultrasound images, to capture the characteristics and nuances of how tissues and/or structures appear on ultrasound. In an embodiment, live ultrasound images may be obtained from one or more databases, and/or in real-time during an ultrasound procedure. The discriminator may include a neural network tasked with distinguishing between live ultrasound images and the synthetic images generated by the generator. In an embodiment, the discriminator may evaluate the quality of the generated images by comparing them to a dataset of real ultrasound images. The goal of the discriminator is to correctly classify whether an image is live or generated. Once a threshold is met, wherein the discriminatory is unable to discern the difference between real data and synthetic data at a certain ratio, the generator is stabilized and ready to produce synthetic simulated data at an acceptable level of "realness."

In further reference to FIG. 1, in an embodiment, training the GAN may include a training process, wherein the training process follows a progression such that the generator creates a simulated ultrasound image, and the discriminator assesses whether the image is realistic or not. The generator and the discriminator may be trained in tandem; the generator improves by trying to "trick" the discriminator, while the discriminator improves by becoming better at distinguishing real from fake images. Over time, this process may aid the generator in producing high-quality synthetic ultrasound images that are virtually indistinguishable from real images. In an embodiment, the generator may receive additional inputs, such as probe position and orientation, tissue type, and/or pathological conditions. Further, a suitable loss function for training the GAN may combine adversarial loss and possibly content loss.

With further reference to FIG. 1, in an embodiment, after generating simulated data, the simulated data may be run through physical models and/or physics-based models to ensure realistic parameters. These models may be designed to simulate real-world phenomena by incorporating the fundamental principles of physics, ensuring that the simulation follows the correct lays of nature. Further, in some embodiments, these models may be integrated with the simulation to ensure realistic parameters.

In further reference to FIG. 1, in a non-limiting example, 3D model 156 may include a 3D voxel occupancy representation (VOR). As used in this disclosure, a "3D voxel occupancy representation (VOR)" of anatomy is a 3D digital representation of a spatial structure of the anatomy, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of a heart. In some cases, voxel may be a smallest distinguishable box-shaped part (i.e., 1px·1px·1px) of a three-dimensional image. In some cases, each voxel of plurality of voxels within VOR may be represented as a cube or rectangular prism (although other shapes may be used in specialized applications). Each voxel may include a size that determines a resolution of the 3D image or model. In an embodiment, smaller voxels may provide higher resolution;

however, it may require more computational resources (e.g., RAM) for at least a processor 108 to process.

Still referring to FIG. 1, each voxel of plurality of voxels within VOR may include one or more embedded values. As used herein, "embedded values" refers to specific numerical or categorical data associated with each voxel. In some cases, embedded values may represent various attributes or characteristics of the corresponding portion of structure that voxel represents. In a non-limiting example, embedded values may include density values, intensity values, texture information, or any other quantitative measures that provide insights into the underlying tissue. Such embedded values may be derived from a set of ultrasonic images or other imaging modalities used to generate data structure. In some cases, embedded values may be utilized, by at least a processor 108, to differentiate between different types of tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

Still referring to FIG. 1, in an embodiment, each voxel of plurality of voxels may include a presence indicator. As used in this disclosure, a "presence indicator" refers to a data element that indicates a presence or absence (i.e., occupancy) of tissue within that portion. In some cases, and without limitation, presence indicators may include an occupancy status as one of the embedded values described herein. Portion may include a specific location within 3D space where data structure is generated; for instance, and without limitation, a coordinate in 3D space represented in a tuple such as (x, y, z). In an embodiment, 3D VOR may provide a spatial framework that allows for the modeling and visualization of structure in 3D space. In some cases, the 3D model 156 may include a plurality of layers or slices (either horizontal [e.g., xy plane] or vertical [e.g., xz or yz plane depends on the view direction]), wherein each layer or slices of the plurality of layers or slices corresponding to a different cross-sectional view of a structure of subject and collectively forming a comprehensive 3D depiction of the structure. In a non-limiting example, 3D VOR having plurality of voxels with presence indicators may indicate whether each voxel in 3D space may be occupied by a part of a structure of subject. A binary value such as 0 or 1 may be configured as presence indicator to show either a pixel of 3D space is occupied (e.g., 1) or empty (e.g., 0). In should be noted that other values may be used as presence indicator such as a Boolean value e.g., TRUE or FALSE.

Still referring to FIG. 1, one or more embedded values, such as, without limitations, occupancy, or density, may be derived from plurality of ultrasonic images described herein by at least a processor 108. In a non-limiting example, determining occupancy status of each voxel of plurality of voxels may include converting set of ultrasonic images to a set of binary images and determining occupancy status of each voxel as a function of the structure of interest's binary value. In some cases, occupancy status may include a value representing the likelihood of occupancy of the corresponding tissue. In another non-limiting example, density may be calculated, by at least a processor 108, for each voxel as a function of the echogenicity of one or more pixels on a given ultrasonic image, wherein, the brightness of the given ultrasonic image may be analyzed since different tissues reflect ultrasound waves differently.

Still referring to FIG. 1, generating 3D model 156 of a subject's organ may include generating a 3D array. In some cases, at least a processor 108 may divide 3D space into a grid of plurality of voxels, each with specific x, y, and z coordinates as embedded values. Each element of 3D array may correspond to a voxel. In some cases, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ultrasonic images of plurality of ultrasonic images.

Still referring to FIG. 1, 3D model 156 of structure may include a 3D grid configured to map presence indicators and/or other embedded values described herein of plurality of voxels (e.g., tissue density, blood flow velocity, echogenicity or acoustic properties, and any other biophysical properties). As used in this disclosure, a "3D grid" refers to a 3D model 156 that divides a given volume (e.g., volume of a structure) into a plurality of discrete units called cells (i.e., volume elements). In an embodiment, each cell within 3D grid may be associated with a distinct voxel. Mapping presence indicators or other embedded values may include assigning each presence indicator or embedded value to each point within 3D grid such as corners of each corresponding cell. Such values may be derived from the plurality of ultrasonic images as described above.

Still referring to FIG. 1, cells may be continuous, meaning that one or more cells may represent one or more continuous regions of space rather than discreate, separate units. In a non-limiting example, instead of being uniform, mapped presence indicator and/or other embedded values may vary continuously across different cells or cell's volume. In such an embodiment, at least a processor 108 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

Still referring to FIG. 1, the 3D model 156 of an organ may include a 3D grid having a plurality of cells e.g., voxels, wherein each cell may contain a continuous range of values representing tissue density, blood flow velocity, or other properties (i.e., embedded values). At least a processor 108 may be configured to apply trilinear or tricubic interpolation to estimate tissue density within each cell based on presence indicator or other known values at the cell's boundaries, since tissue densities change gradually; Such 3D grid may provide a smooth, continuous representation of heat's internal structures, allowing for more nuanced analysis and visualization as described below. In a further embodiment, 3D grid with continuous cells may be additionally used in fluid dynamics simulations.

Still referring to FIG. 1, presence indicators and/or other embedded values may be mapped to a 3D grid as a function of array masking. In a non-limiting example, at least a processor 108 may generate a mask e.g., a binary array that defines which voxels or cells are affected. A mask may be used to select or modify specific voxels or cells based on certain attributes; for instance, and without limitation, at least a processor 108 may use a mask to isolate the LA within the heart focusing the analysis on that specific region. Such a mask may include criteria defined by specific density thresholds that distinguish the LA's tissue (i.e., voxels representing LA in 3D grid) from surrounding structures (i.e., neighboring voxels). In some cases, such mask may further include a binary mask, wherein each voxel in the 3D grid may be assigned a first presence indicator such as 1 if the voxel meets the criteria for the LA and a second presence indicator such as 0 if it does not. In some embodiments, a mask may be directly applied to a 3D grid, selecting, or modifying voxels or cells, thereby enabling at least a processor 108 to highlight, exclude, or otherwise manipulate specific parts of a heart within 3D grid. At least a processor 108 may then perform an element-wise multiplication between 3D grid and the mask. Continuing from the previous non-limiting example, voxels corresponding to the LA (wherein the mask value is 1) may retain their original values, while other voxels (where the mask value is 0) may be set to 0 or other specific value (i.e., excluded or masked out).

Still referring to FIG. 1, in some embodiments, 3D grid may include one or more spatial features extracted from plurality of ultrasonic images. As used in this disclosure, "spatial features" are specific characteristics or attributes related to the spatial arrangement, shape, size, texture, or orientation of structures within a 3D space. In some cases, spatial features may include one or more embedded values described herein and their combinations thereof. In a non-limiting example, spatial features may be represented numerically as a vector, a metric or other mathematical constructs that capture specific spatial characteristics. In some cases, spatial features may also be visualized as contours, surfaces, or other geometric representations. In an embodiment, spatial features may be extracted using edge detection, texture analysis, or other image processing techniques (e.g., cleaning and enhancing images, image segmentation, and/or the like). In another embodiment, one or more machine learning models, such as convolutional neural networks (CNNs) as described in further detail below, may be used to extract complex spatial features.

Still referring to FIG. 1, in a non-limiting example, one or more spatial features may include one or more shape features (i.e., characteristics related to the shape of specific structures), such as curvature, surface area, volume, and/or the like. In another non-limiting example, one or more spatial features may include one or more texture features (i.e., characteristics related to the texture or pattern within tissues, as seen in plurality of ultrasonic images), such as gray-level co-occurrence matrix (GLCM) features representing the texture of heart muscle tissue. In another non-limiting example, one or more spatial features may include one or more orientation features (i.e., characteristics related to the orientation or alignment of structures), such as the angle or alignment of the septum within the heart. In a further non-limiting example, one or more spatial features may include one or more edge and boundary features (i.e., Characteristics related to the edges or boundaries between different structures), such as edge detection features highlighting the boundary between the myocardium and the cardiac chambers. As an ordinary person skilled in the art, upon reviewing the entirety of this disclosure, will be aware of various spatial features extracted from plurality of ultrasonic images consistent with this disclosure.

With continued reference to FIG. 1, at least a processor 108 may be configured to compute, using a reward function, the visibility score by identifying, using at least a processor 108, at least a key structure of ultrasound data 128, comparing, using at least a processor 108, a representation of the key structure of ultrasound data 128 to a corresponding representation in a target canonical view, and generating, using at least a processor 108, the visibility score as a function of the comparison. As used in this disclosure, "key structure" is an anatomical component within an image that serves as a reference point for analysis. The at least a key structure may include organs, tissues, bones, blood vessels, and/or other relevant features that are critical for diagnostic accuracy, procedural guidance, computational modeling, and the like. The identification of the at least a key structure may involve image segmentation, feature extraction, or machine learning-based recognition. As used in this disclosure, "representation" is a data-derived depiction of a portion of a view that encapsulates characteristics for comparison. The representation may include spatial, visual, or mathematical attributes extracted from an image, such as intensity values, shape contours, segmentation masks, or reconstructed 3D models. In the context of imaging, a representation 154 may correspond to a subset of a view, highlighting key structures 152 or reference points for evaluation.

Still referring to FIG. 1, in an embodiment, at least a processor 108 may be further configured to display, at user interface 180, a position of virtual sensor relative to 3D model 156 as a function of probe position data 136. For purposes of this disclosure, a "user interface" is a means through which a user and a computer system interact. The goal of a UI may include allowing a user to effectively control and interact with a system, software application and/or device. In one or more embodiments, user interface 180 may include a graphical user interface (GUI). A "GUI," as used herein, is a visual interface that allows users to interact with electronic devices through graphical elements rather than text-based commands. Features of a GUI may include, but are not limited to windows, icons, menus, buttons, sliders and controls, and/or any other graphical content configured to assist a user in interacting with an electronic device. As used in this context, "manipulation" refers to actions or interactions a user may perform to modify, control, or navigate through an interface. Such manipulations may require the use of input devices such as, but not limited to mouses, keyboards, and/or touchscreens. For example, manipulations may include clicking, dragging, scrolling, resizing, zooming, hovering, right-clicking, keyboard shortcuts, inputting data, removing data, and/or modifying data.

In continued reference to FIG. 1, in an embodiment, GUI may include one or more event handlers. As used throughout this disclosure, "event handler" refers to functions or methods designed to respond to specific events in a program, particularly in user interface 180 contexts. An "event" is an occurrence that is detected by the program. For example, this may include a mouse click, keyboard input, and/or a change in a form field. In an embodiment, event handlers may include a listener and or binding process. A listener is a function that listens for specific events on an element. For instance, a button or an input field. A binding process is the process of associating an event with its handler. When an event occurs, an event object may be passed to the handler, containing details about the event. Event handlers allow for interactivity, modularity, and reusability. In such that, event handlers enable applications to respond dynamically to user actions, organize code by separating event handling logic from other program logic, and the same handler may be used for multiple elements and/or events. Further, in an embodiment, the feedback from an event handler may be utilized as training data in the training or retraining of models and/or modules as described here within.

Continuing to reference FIG. 1, in an embodiment, GUI may be displayed at a display device 184. As used herein, a "display device" refers to an electronic device that visually presents information to the entity. In some cases, display device 184 may be configured to project or show visual content generated by computers, video devices, or other electronic mechanisms. In some cases, display device 184 may include a liquid crystal display (LCD), a cathode ray tube (CRT), a plasma display, a light emitting diode (LED) display, and any combinations thereof. In a non-limiting example, one or more display devices may vary in size, resolution, technology, and functionality. Display device 184 may be able to show any data elements and/or visual elements in various formats such as, textural, graphical, video among others, in either monochrome or color. Display device 184 may include, but is not limited to, a smartphone, tablet, laptop, monitor, tablet, and the like. Display device 184 may include a separate device that includes a transparent screen configured to display computer generated images and/or information. In some cases, display device 184 may be configured to present a GUI to a user, wherein a user may interact with the GUI. In some embodiments, GUI may be updated based on user inputs and/or movements of catheter 120.

With continued reference to FIG. 1, in an embodiment, at least a processor 108 is configured to determine, using movement vector 144, real-time guidance data 160. As used throughout this disclosure, "real-time guidance data" refers to information that is provided to assist in decision-making in an ultrasonic procedure. In an embodiment, real-time guidance may be continuous and/or instantaneous. Meaning that some form of real-time guidance may be present throughout the duration of a procedure. Real-time guidance data 160 may assist a user in accurately capturing a canonical view of a target area. In an embodiment, real-time guidance data 160 may indicate an optimal movement 164 of catheter 120 as predicted by scoring-based canonical view simulation model 140. For purposes of this disclosure, an "optimal movement" refers the most efficient, effective, or safe adjustment of the ultrasound device to capture a desired canonical view. An optimal movement 164 is determined by aligning the device's simulated position with canonical views that meet predefined diagnostic criteria based on historical canonical view data.

In further reference to FIG. 1, in an embodiment, at least a processor 108 is configured to display the real-time guidance data 160 to a user through user interface 180. At least a processor 108 may dynamically render real-time guidance data 160, such as visual cues, performance metrics 188, and directional indicators, onto a display, enabling the clinician to continuously monitor and adjust catheter's 120 position and orientation to achieve optimal canonical views. This real-time feedback may include overlays on anatomical images, graphical representations of catheter 120 movement, and quantitative performance assessments that compare current actions against the ideal movement predicted by scoring-based canonical view simulation model 140. Additionally, user interface 180 may support multimodal feedback by integrating auditory or haptic signals, further assisting the clinician in fine-tuning device positioning during the procedure.

With further reference to FIG. 1, in an embodiment, real-time guidance data 160 may include one or more of visual feedback 168, auditory feedback 172, and/or haptic feedback 176. As used herein, "visual feedback" refers to information received through one's sense of sight to help guide, adjust, or improve one's movements or interactions. For example, visual feedback 168 may include overlays indicating optimal probe orientations to achieve canonical views, color-coded feedback reflecting the quality of captured images, grid or overlay patterns, real-time positioning feedback, distance or coverage indicators, feedback for depth control, real-time image or slice views, warning indicators, and/or user interface 180 controls. In an embodiment, visual feedback 168 may include an on-screen visual guide. For purposes of this disclosure, an "on-screen visual guide" is a dynamic graphical overlay integrated into an ultrasound imaging display that provides real-time, intuitive cues to assist the operator in capturing optimal canonical views. The on-screen visual guide may include directional arrows, distance markers, color-coded regions, and anatomical landmark indicators that visually depict the current probe position relative to the target area. By illustrating recommended adjustments, such as changes in angle, orientation, or position, the on-screen visual guide may help ensure that the ultrasound device is aligned to capture high-quality, diagnostically valuable images.

In continued reference to FIG. 1, in an embodiment, at least a processor 108 may be configured to display, through user interface 180, ultrasound data 128 as an ultrasound image and overlay, on the ultrasound image at user interface 180, real-time guidance, wherein real-time guidance includes visual feedback 168 configured to direct a user in real-time to adjust catheter's 120 position. For instance, real-time guidance overlay may comprise directional arrows, color-coded indicators, and performance metrics 188 derived from scoring-based canonical view simulation model 140, which assesses the current image against predefined diagnostic standards. By integrating this overlay, system 100 may enable clinicians to intuitively interpret the relationship between catheter's 120 current position and the target canonical view, thereby facilitating precise adjustments during the procedure.

In continued reference to FIG. 1, "auditory feedback," as used throughout this disclosure, refers to information received through one's sense of hearing that helps guide, adjust, or improve one's movements or interactions. For example, auditory feedback 172 may include beeps or tones for positioning adjustments, continuous feedback indicating progress toward capturing a canonical view, including progressive beeps or tones and/or continuous sounds signaling active imaging areas, volume and tone variations corresponding to image quality, directional cues, alert sounds for system warnings, confirmation sounds for completed tasks, interactive sounds for user engagement, and/or the like. For purposes of this disclosure, "haptic feedback" refers to information received through one's sense of touch or tactile sensation to provide guidance that helps adjust or improve one's movements or interactions. For example, haptic feedback 176 may include vibrations that guide positioning and alignment toward optimal canonical views, vibrations for depth control, signals corresponding to progress in achieving canonical views, obstacle detection and contact feedback, guidance for precise movement adjustments, error or alert signals, feedback on consistency and image quality, and/or the like. In one or more embodiments, one or more of these exemplary feedback mechanisms may be used in parallel to assist in capturing high-quality canonical views.

With continued reference to FIG. 1, in an embodiment, real-time guidance data 160 may include a set of visual indicators, wherein the set of visual indicators shows the relative alignment of catheter 120 with respect to a target canonical view. Further, at least a processor 108 may be configured to update the set of visual indicators as a function of one or more movements of catheter 120. The set of visual indicators may be dynamic, continuously updating as catheter 120 moves, and may offer immediate feedback to a clinician regarding catheter's 120 position and orientation relative to the target canonical view, which corresponds to a specific anatomical configuration of an organ, blood vessel, or other anatomical feature. In an embodiment, the set of visual indicators may take various forms, such as color-coded graphics, proximity bars, and directional arrows, each indicating how close the catheter's 120 current imaging angle is to achieving the desired canonical view. For instance, system 100 might use a color gradient with green indicating optimal alignment with the canonical view, yellow for moderate alignment, and red for positions requiring further adjustment. Additionally, system 100 could employ a graphical map or 3D model 156 of the anatomy to represent catheter's 120 movements and the corresponding location of key anatomical landmarks in real time. In this context, a target canonical view may include an ideal imaging perspective and/or key target point that defines the optimal view for diagnostic or therapeutic purposes.

In further reference to FIG. 1, in an embodiment, at least a processor 108 may be configured to update real-time guidance data 160 as a function of one or more changes in ultrasound data 128 and probe position data 136. For example, at least a processor 108 may integrate data from ultrasound data 128 and probe position data 136, to track catheter's 120 position and orientation within the body. At least a processor 108 may analyze catheter's 120 movement data, adjusting the set of visual indicators accordingly to reflect real-time changes in catheter's 120 location. This may ensure that clinicians receive up-to-date guidance, which may be crucial for making precise adjustments during procedures such as catheter insertion, ablation, or biopsy.

With further reference to FIG. 1, in an embodiment, real-time guidance may include a performance metric 188, wherein performance metric 188 is determined as a function of comparing a user's actions against an optimal movement 164 predicted by scoring-based canonical view simulation model 140. For purposes of this disclosure, a "performance metric" is a metric that quantitatively evaluates the effectiveness of a user's actions relative to an optimal movement 164 predicted by the scoring-based canonical view simulation model 140. In an embodiment, performance metric 188 may be derived by comparing the current catheter position, orientation, and imaging quality against the ideal parameters defined by the canonical view, effectively measuring the deviation from the optimal imaging configuration. For instance, performance metric 188 could incorporate factors such as alignment accuracy, the efficiency of movement toward the target canonical view, and the quality of the captured image, thereby providing a comprehensive assessment of procedural performance. Moreover, in an embodiment, performance metric 188 may be displayed on the user interface 180 in real time, allowing clinicians to receive immediate feedback and make prompt adjustments to enhance procedural outcomes.

Figure 2A:
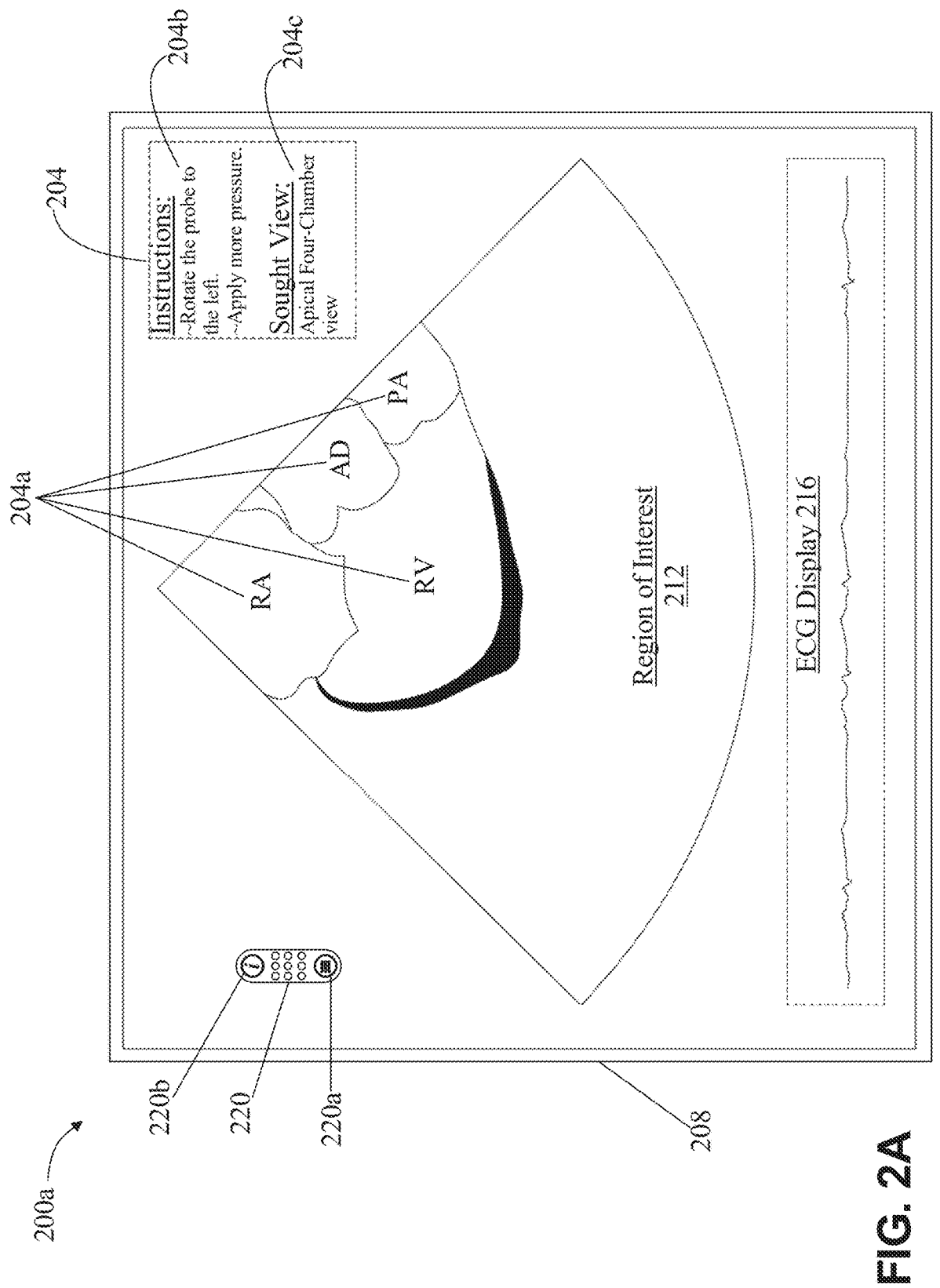
FIG. 2A is an exemplary graphical user interface displaying the real-time guidance generated by a system for guiding ultrasonic probe positioning using scoring-based canonical view simulation model.

Now referring to FIG. 2A, illustrated is an exemplary graphical user interface 200a displaying real-time guidance 204 generated by a scoring-based canonical view simulation model. In an embodiment, graphical user interface 200 may be displayed at a display device 208. Further, graphical user interface 200 may display a region of interest 212 overlaid with real-time guidance 204. In some embodiments, real-time guidance 204 may include on-screen guidance 204a, which may aid a user in identifying one or more regions displayed in a region of interest 212. In one or more embodiments, real-time guidance may include a window that may display one or more adjustment recommendations

204b, a sought view 204c, and/or adherence metrics with an optimal canonical view. Further, in some cases, graphical user interface 200 may include an ECG display 216, wherein graphical user interface 200 may display an ultrasound image, a 3D model, and/or ECG data. Specifically, for example, ECG data may be displayed at ECG display 216. In some embodiments, 3D model may be displayed in graphical user interface 200.

In continued reference to FIG. 2A, in an embodiment, graphical user interface 200 may include a menu bar 220. In some cases, menu bar 220 may be moved to different areas of the display. For example, if menu bar 220 blocks a view, a user may click and drag menu bar 220 to another portion of the display. In an embodiment, menu bar 220 may include a menu button 220a and/or an information button 220b. Menu button 220a may allow a user to toggle into different views, and/or tools wherein each of the views and/or tools correspond to real-time guidance 204. For example, a user may toggle into menu button 220a and click into a view with an on-screen guidance overlay configured to guide a user to an optimal canonical view, wherein the overlay includes a grid and/or a colored line that is meant to be followed. Menu button 220a may also allow a user to adjust other real-time guidance 204, such as auditory feedback, haptic feedback, and/or other visual feedback. In an embodiment, information button 220b may allow a user to toggle into a pop-up window that displays metadata of the current procedure. For example, this may include ultrasound settings, time data, progress data, adherence data, and/or the like.

Figure 2B:
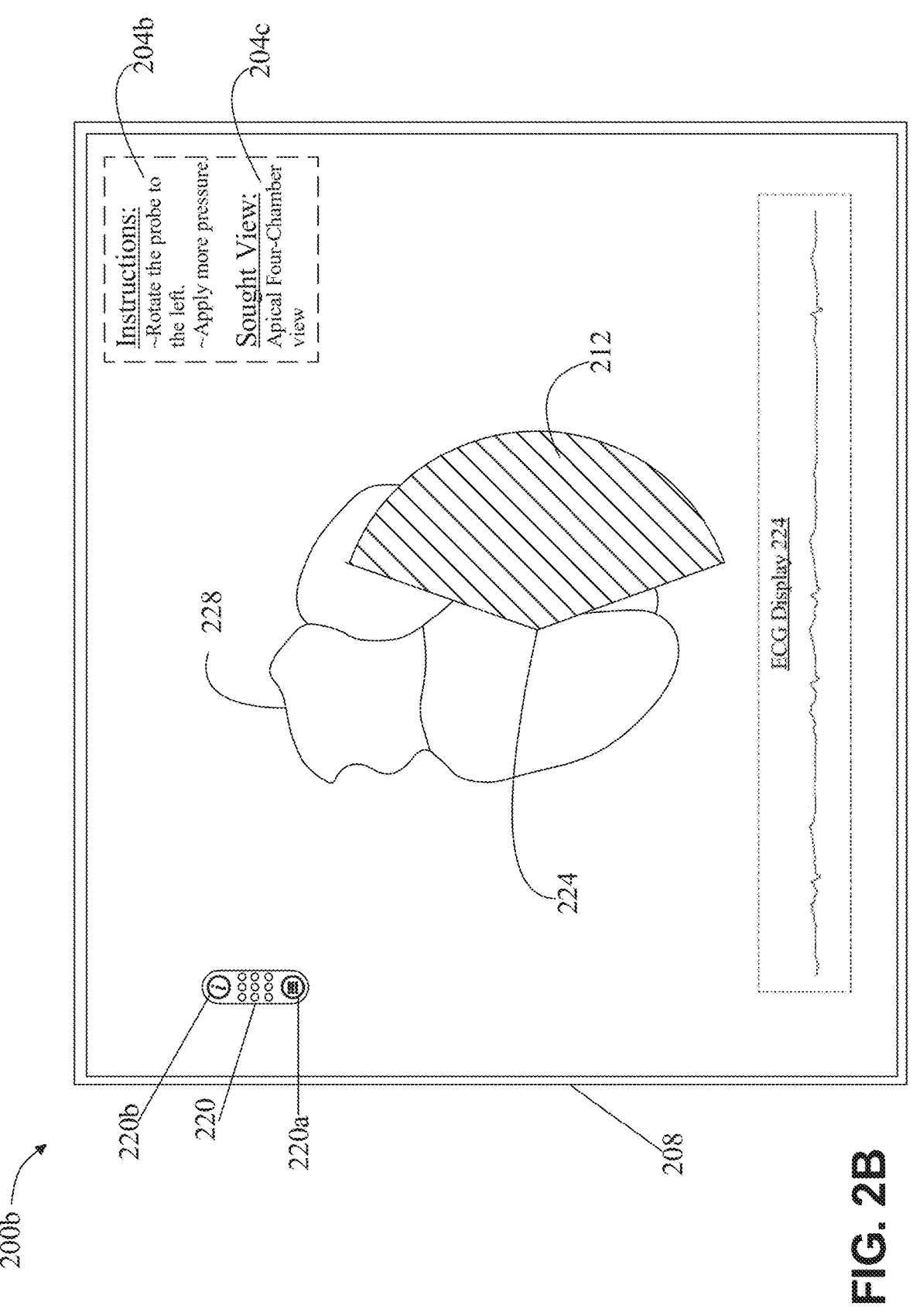
FIG. 2B is an exemplary graphical user interface displaying the real-time guidance generated by a system for guiding ultrasonic probe positioning using scoring-based canonical view simulation model.

Referring now to FIG. 2B, illustrated is an exemplary graphical user interface 200b displaying real-time guidance 204 generated by a scoring-based canonical view simulation model. Graphical user interface 200b displays many of the components discussed in reference to FIG. 2A and illustrated by graphical user interface 200a. However, graphical user interface 200b displays a different view, specifically graphical user interface 200b displays a position of virtual sensor 224 relative to 3D model 228. This view may be toggled between, aiding a user to view both more detailed views as well as broader views. In some embodiments, real-time guidance 204 may overlay 3D model 228. This may include grids, color coding, arrows, lines, and/or the like, and may aid a user in capturing an optimal canonical view in the region of interest 212.

Figure 3:
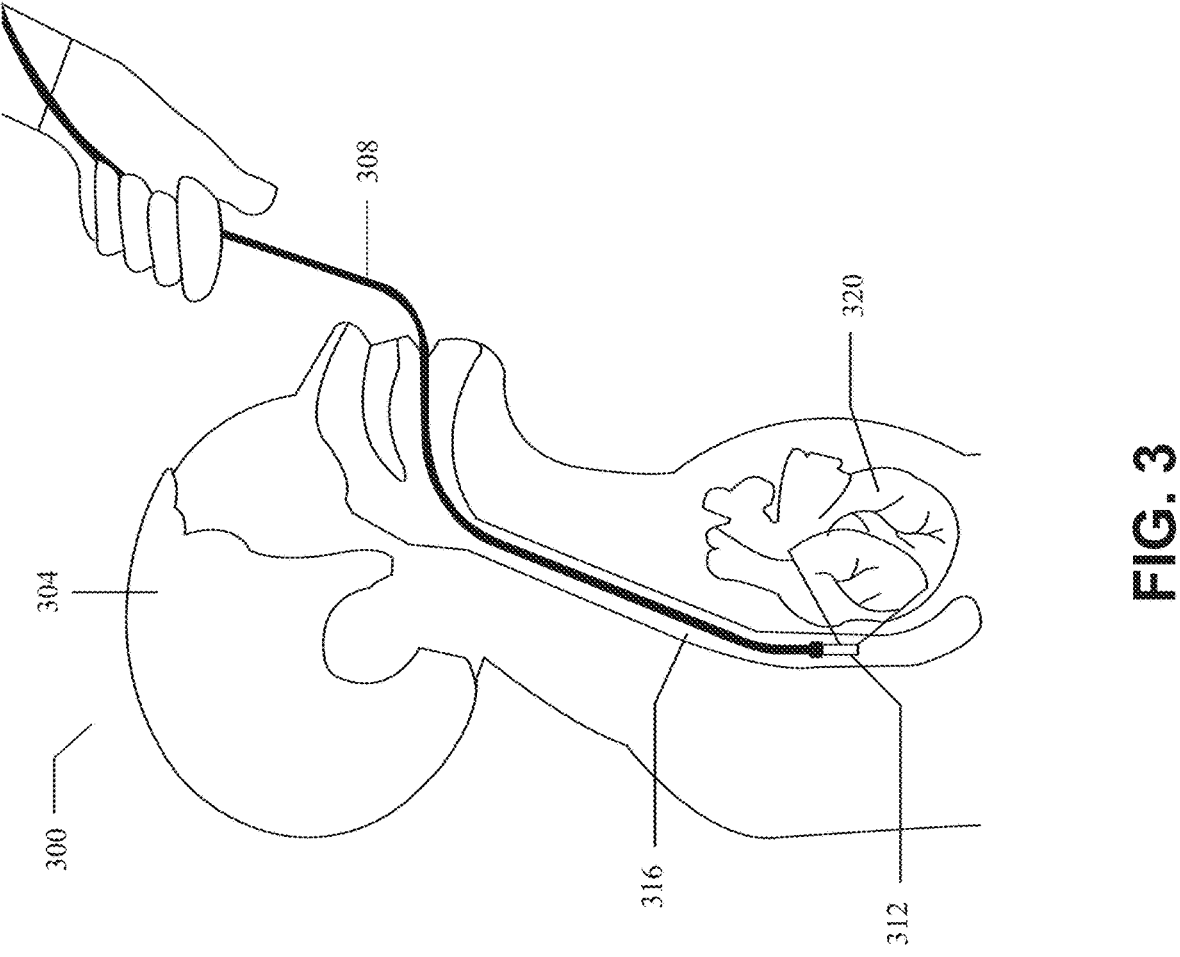
FIG. 3 is a schematic diagram of an exemplary transesophageal echocardiogram (TEE)

Now referring to FIG. 3, a schematic of an exemplary transesophageal echocardiogram (TEE) procedure 300 is shown. In some cases, TEE 300 may be performed during another procedure for instance heart surgery. According to some embodiments, a patient 304 has an endoscope 308, with an ultrasonic transducer 312, inserted into his esophagus 316. As one's esophagus 316 is proximal one's heart 320, ultrasonic transducer 312 may generate echocardiograms.

Still referring to FIG. 3, in some embodiments, transesophageal echocardiography (TEE) may provide superior imaging quality than intracardiac echocardiography (ICE), as larger ultrasound transducers 312 may be placed within the esophagus 316 than within heart 320. In some cases, ultrasound transducers must be substantially miniaturized to fit within heart 320, as in ICE catheters. As esophagus 316 may be proximal to heart 320, TEE may provide a clear image of various heart structures without needing vascular access (as commonly required by ICE). Additionally, TEE may be performed without obstructing patient's 304 ribcage and intermediary tissues (as commonly required by transthoracic echocardiography [TTE]). In some cases, TEE images may also provide information associated with angle of acquisition. Angle of acquisition may be an angle of TEE probe with respect to esophagus 316 (e.g., esophageal axis).

Figure 5:
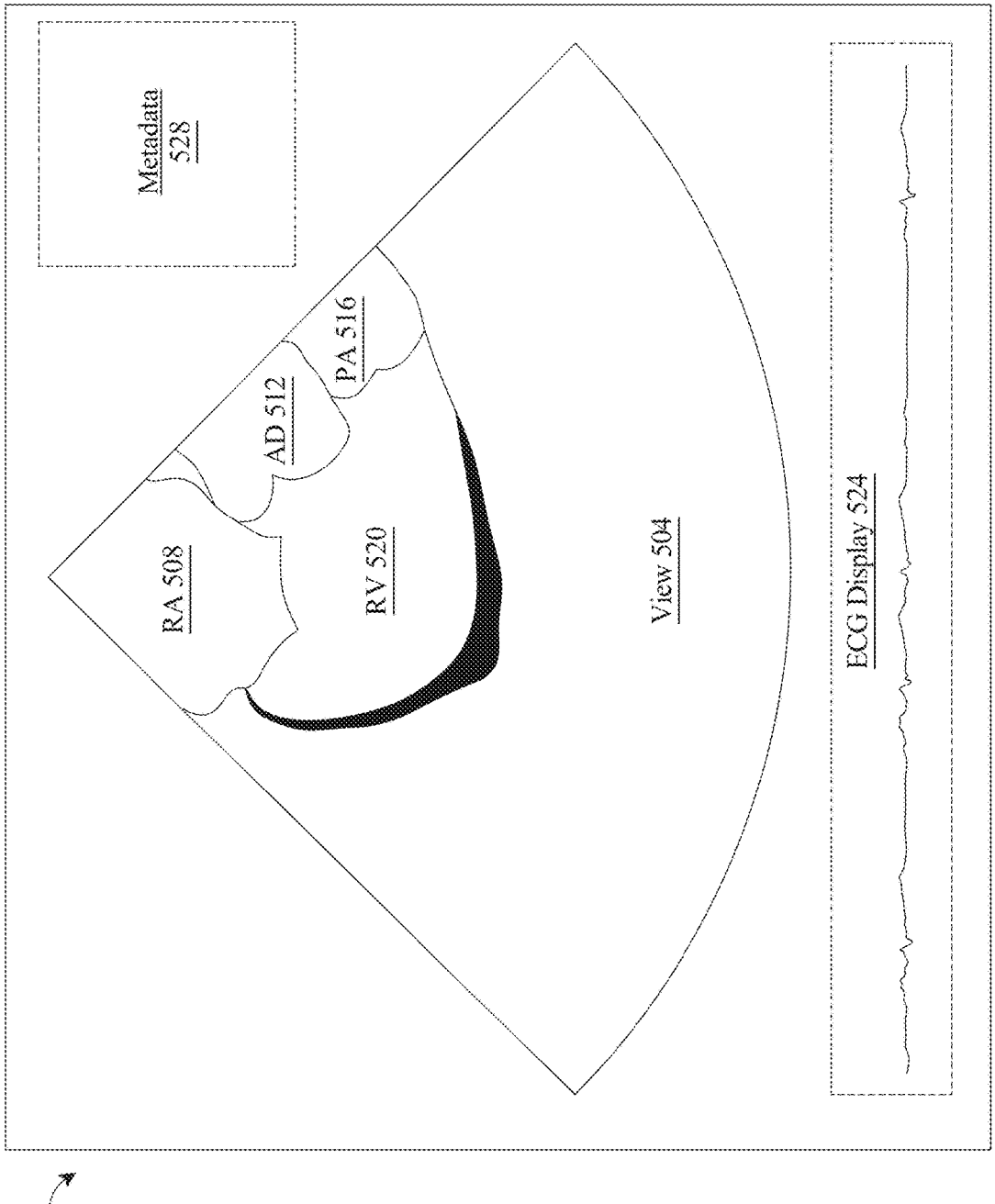
FIG. 5 shows an exemplary embodiment of an intracardiac echocardiography (ICE) image.
Figure 6:
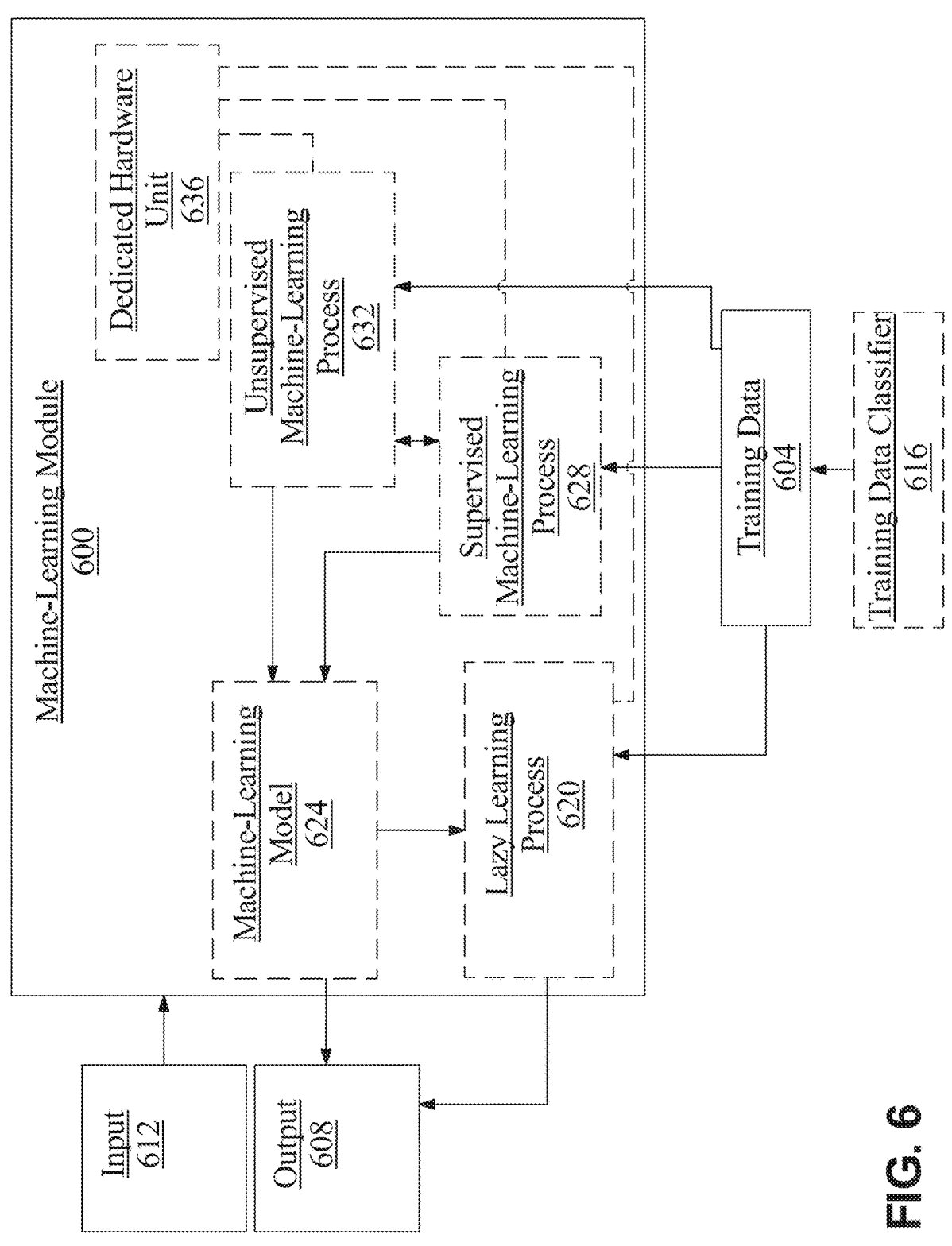
FIG. 6 is a block diagram of an exemplary embodiment of a machine learning model.
Figure 7:
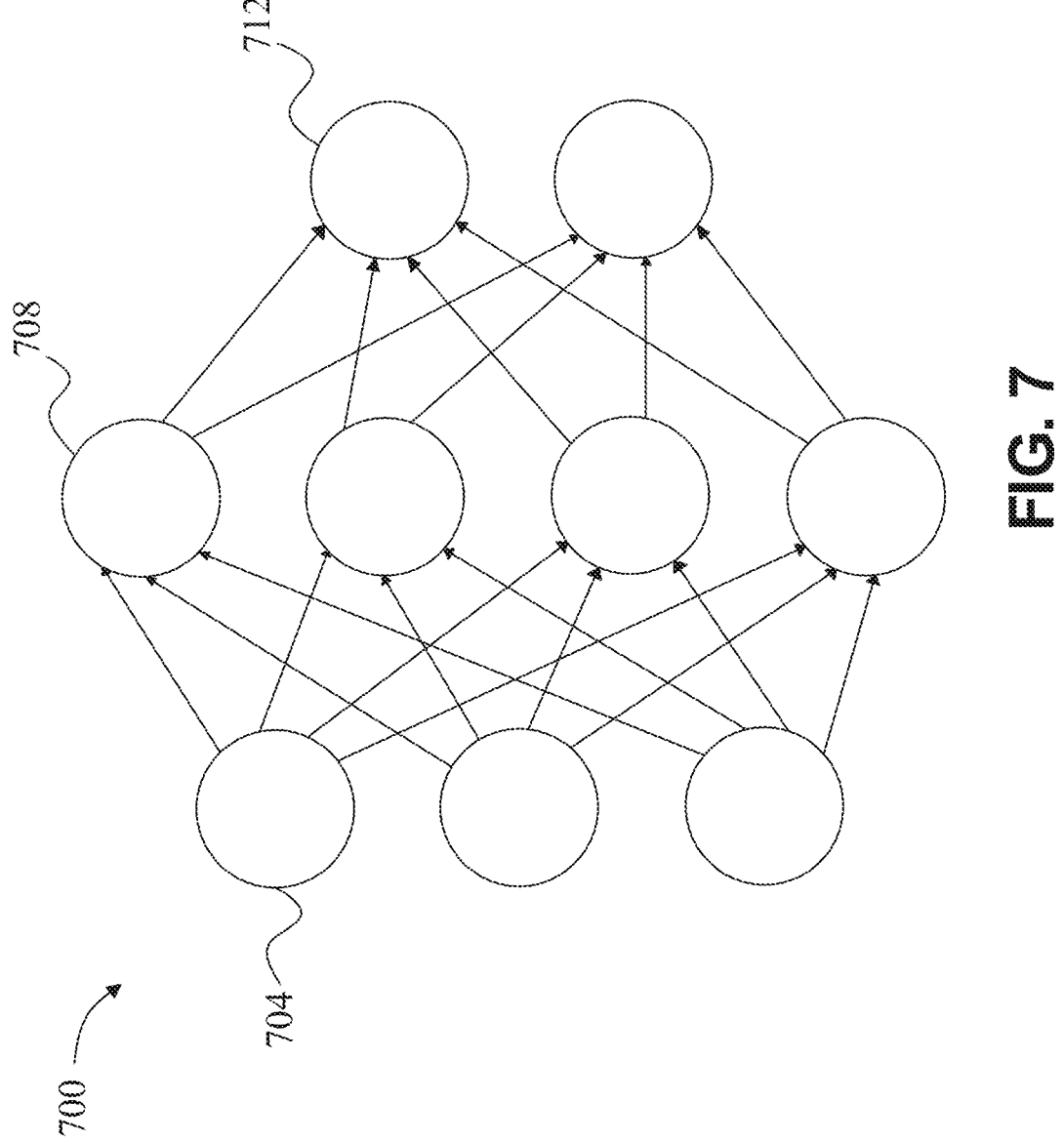
FIG. 7 is a schematic diagram of an exemplary embodiment of a neural network.

Still referring to FIG. 3, in some embodiments, TEE echocardiogram data, including images showing heart structures and, in some cases, angle of acquisition, may be used as input to any machine learning process described in this application, for instance with reference to FIGS. 5-7. For instance TEE echocardiogram data may be used to reconstruct 3D heart models. In some cases, TEE echocardiogram data is input into a machine learning model that outputs a 3D heart model (e.g., 3D mesh model and/or statistical shape model).

Still referring to FIG. 3, in some embodiments, TEE may be a preferred imaging modality for structural heart interventions, such as without limitation left atrial appendage occlusion (LAOO) and aortic/mitral/other heart valve replacement procedures. In some cases, technology and improvements described in this disclosure permit creation and/or modification of a 3D heart mesh from TEE data to aid in planning implant size selection, as well as to guide implantation procedures. In some cases, virtual placement of a 3D model of a candidate implant (such as without limitation LAAO device and/or heart valve implants) can be simulated on a 3D heart model generated by any method described in this disclosure. This novel and improved functionality may validate appropriate size and placement of implants within heart 320, as well as other organs within body of patient 304. For example, in the context of electrophysiology procedures, TEE 300 can be used to create heart anatomical models that can be used as reference for electroanatomic mapping, and guidance of ablation catheters for atrial fibrillation procedures (such as without limitation pulmonary vein isolation).

Still referring to FIG. 3, in some embodiments, applications described with reference to TEE 300 above can be extended for use with TTE and point of care ultrasound (POCUS). In some cases, both TTE and POCUS may acquire ultrasound images of chest/surface of patient 304. In some cases, TTE and POCUS data may be used as an input (and/or training data) for any machine learning process described in this disclosure, for instance with reference to FIGS. 5-7. In some cases, use of TTE and/or POCUS data (in machine learning processes described in this disclosure) may require adjustment in ultrasound acquisition parameters and positions to acquire a sufficient number of frames for 3D reconstruction. In some cases, TTE and POCUS offer improved accessibility (with POCUS being portable/mobile as well) and non-invasive 3D heart modeling, often without anesthesia or sedation, compared to catheterized 3D heart modeling commonly performed today for electroanatomical mapping and ablation procedures.

Figure 4:
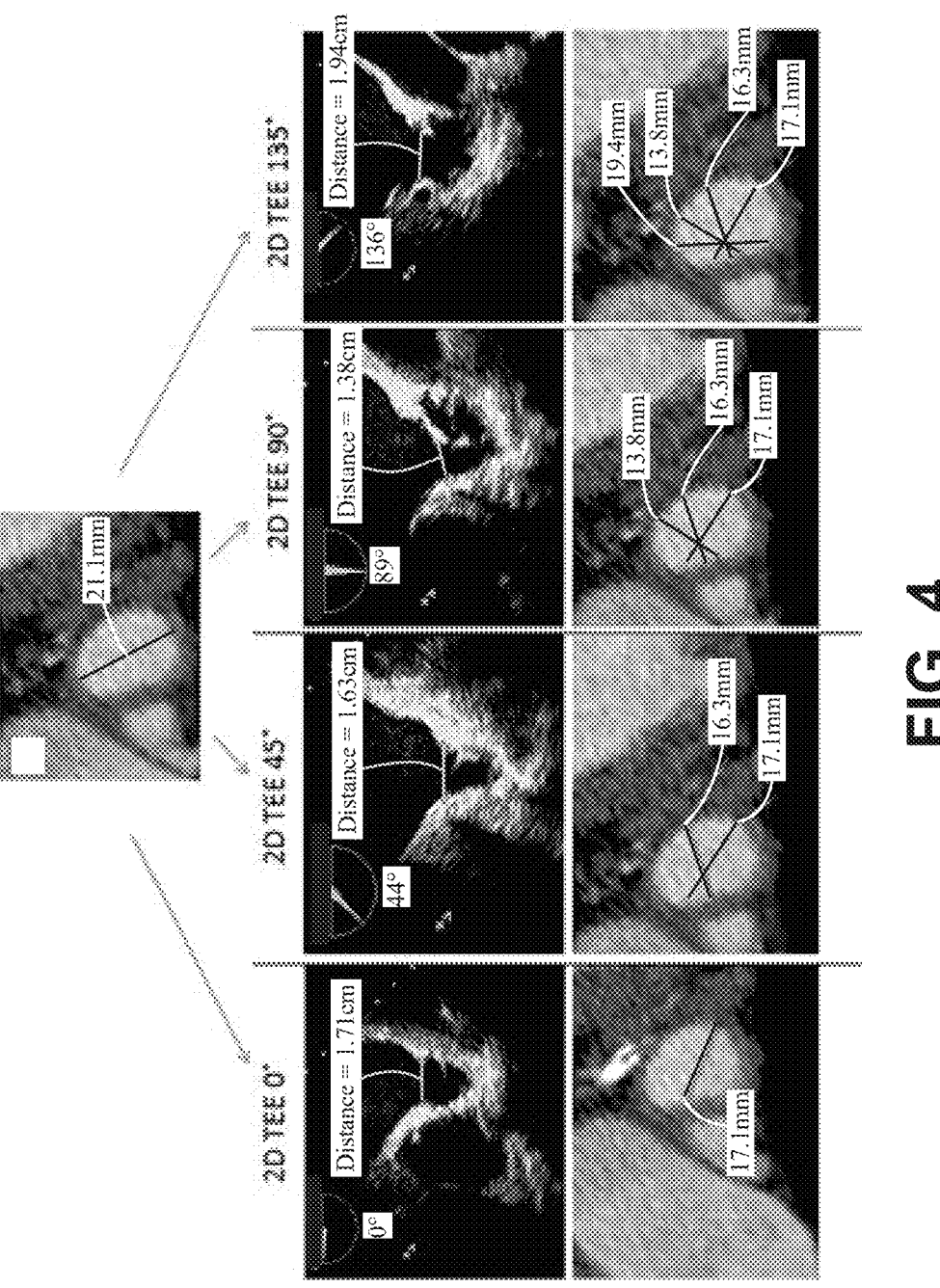
FIG. 4 is a set of 2D transesophageal echocardiogram (TEE) views at varying orientations.

Referring now to FIG. 4, multiple 2D transesophageal echocardiogram (TEE) views at varying orientations are presented. Image A demonstrates a maximal LAA diameter of 21.1 mm obtained utilizing the double-oblique multiplanar reconstruction methodology by 3D CT. Panels B-E demonstrate the traditional 2D TEE LAA scanning views of 0°, 45°, 90°, and 135° views reflected on a multiplanar reconstruction of the LAA ostium on 3D CT. In panels F-I, the CT dimensions are taken at a focal intersection point and angled, from 0° (assigned as the measurement of 17.1 mm), and increased by 45° around this focal point for each subsequent measurement. Panel I demonstrate in this patient the 135° TEE measurement of 19.4 mm as off-axis to the true centroid of the LAA, and is not reflective of the maximal LAA width as shown in panel A, thereby resulting in an undersized WATCHMAN device. By CT, this patient would receive a 24 mm device with no peri-watchman leak.

Now referring to FIG. 5, an exemplary embodiment of an ultrasonic image such as ICE image 500 is illustrated. As described above with reference to FIG. 1, plurality of ultrasonic images may include a plurality of ICE images, wherein each ICE image of the plurality of ICE images is a specialized form of echocardiography that may provide detailed image of heart's interior structures. In a non-limiting example, plurality of ICE images may include an ICE video (e.g., plurality of ICE images arranged in a corresponding time sequence). In an embodiment, ICE image 500 may be real-time, dynamic ultrasound image that provide a (detailed) view 504 of heart's interior structures, including, without limitation, right atrium (RA) 508, anterior descending (AD) 512, pulmonary atresia (PA) 516, and right ventricular (RV) 520.

With continued reference to FIG. 5, in some cases, ICE image 500 may include gray scaled image. It should be noted that, in some cases, ICE image 500 may be configured to visualize blood flow and/or blood flow patterns within the heart via color doppler. In some cases, resolution and/or clarity of ICE image 500 as described herein may be superior to transthoracic or transesophageal echocardiography due to the ICE catheter may be positioned inside the heart, closer to the structures being imaged.

Still referring to FIG. 5, in a non-limiting example, heart chambers may appear as dark, anechoic (black) areas since they are filled with blood, which doesn't reflect ultrasound waves well. Heart walls, valves, and/or other structures may appear as varying shades of gray, depending on their density and composition, in some cases, Color Doppler overlays may show blood flow in different colors, indicating the direction and speed of blood flow. For instance, and without limitation, red may indicate flow towards the probe, while blue may indicate flow away from the probe.

With continued reference to FIG. 5, in a non-limiting embodiment, ICE image 500 may be synchronized with ECG data, allowing for precise timing of cardiac events with anatomical visualization provided by ICE. In some cases, ICE image 500 may include an ECG display 524 configured to display ECG waveform as a continuous line graph at the top, bottom, or side of ICE image 500. In some cases, specific parts of the cardiac cycle e.g., systole or diastole, may be correlated with visual data from ICE image 500.

Additionally, or alternatively, and still referring to FIG. 5, ICE image 500 may come with accompanying metadata 528 displayed on the side or corners of ICE image 500 as described herein. In some cases, metadata 528 may provide essential contextual information about ICE image 500 and/ or the corresponding patient. In a non-limiting example, metadata 528 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace (e.g., ECG data as described above), measurement annotations (e.g., any measurements taken directly on the image e.g., diameter, a value of thickness of a heart wall and the like), image sequence information (e.g., image number, total number of frames, and the like), comments or notes, hospital or clinic information, and/or the like. As an ordinary person skilled in the art, upon reviewing the entirety of this disclosure, will be aware of ICE image 500 and various components thereof may be incorporated by system 100 for generating 3D model of cardiac anatomy.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example inputs may include ultrasound data, probe position data, and/or user input. Whereas outputs may include a movement vector, an optimal movement, visual feedback, auditory feedback, haptic feedback, and/or a performance metric.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to cohorts related to specific canonical views, wherein paired CT data and ultrasound data correspond to such a canonical view and or associated parameters.

Still referring to FIG. 6, a computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)±P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 6, a computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 6, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 6, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 6, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 6, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}\!:\!X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation o of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25th percentile value and the 50th percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 6, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632 may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
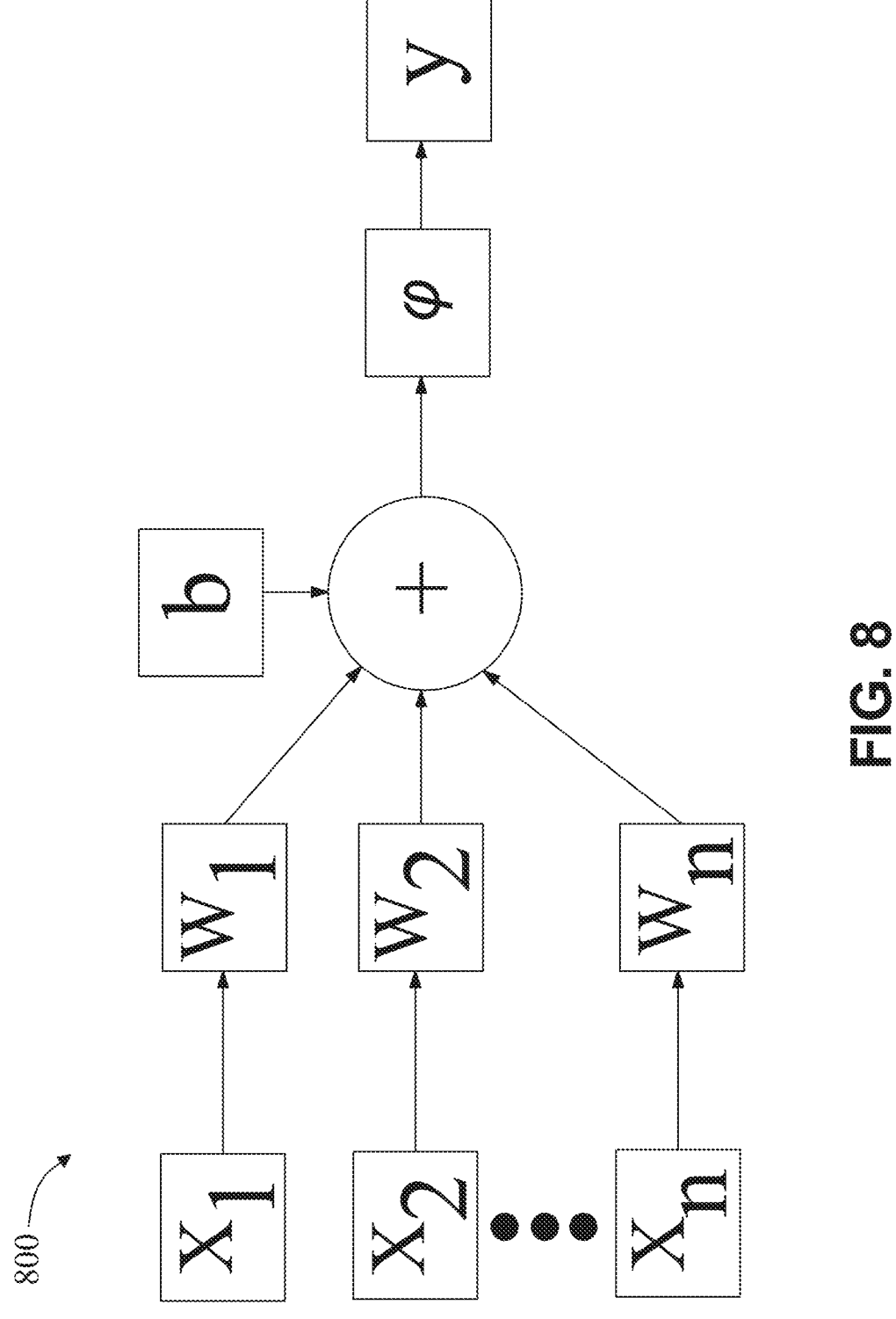
FIG. 8 is a schematic diagram of an exemplary embodiment of a neural network node.

Referring now to FIG. 8, an exemplary embodiment of a node 800 of a neural network is illustrated. A node may include, without limitation a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form

42

$$f(x) = \frac{1}{1 - e^{-x}}$$

given input x, a tanh(hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are xi, a swish function such as $f(x)=x*\text{sigmoid}(x)$, a Gaussian error linear unit function such as $f(x)=a(1+\tanh(\sqrt{2/\pi}\,(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function o, which may generate one or more outputs y. Weight $w_i$ applied to an input xi may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring now to FIG. 9, an exemplary method 900 for guiding ultrasonic probe positioning using a scoring-based canonical view simulation model is illustrated. Method 900 may include a step 905 of receiving, from at least a transducer, ultrasound data. This may be implemented, without limitation, as referenced in FIGS. 1-8.

In continued reference to FIG. 9, method 900 may include a step 910 of detecting, using a localization system, probe position data as a function of a location of a catheter, wherein the catheter is coupled to the at least a transducer. This may be implemented, without limitation, as referenced in FIGS. 1-8.

With further reference to FIG. 9, method 900 may include a step 915 of receiving, by at least a processor, ultrasound data and probe position data. In an embodiment, ultrasound data and probe position data may include live data. Further in some cases, the ultrasound data and probe position data may be received from a real ultrasonic procedure. This may be implemented, without limitation, as referenced in FIGS. 1-8.

In continued reference to FIG. 9, method 900 may include a step 920 of generating, using a scoring-based canonical view simulation model, a movement vector as a function of the ultrasound data and the probe position data. In an embodiment, the scoring-based canonical view simulation model may include a reinforcement learning model trained using computed tomography (CT) data. This may be implemented, without limitation, as referenced in FIGS. 1-8.

With further reference to FIG. 9, method 900 may include a step 925 of determining, using the movement vector, real-time guidance data. In an embodiment, real-time guidance data may indicate an optimal movement of a catheter as predicted by the scoring-based canonical view simulation model and may include one or more of visual feedback, auditory feedback, and/or haptic feedback. In an embodiment, real-time guidance data may include a performance metric, wherein the performance metric is determined as a function of comparing a user's actions against an optimal movement predicted by the scoring-based canonical view simulation model and the performance metric is displayed, at the user interface, in real-time. In an embodiment, step 925 may further include displaying, through the user interface, the ultrasound data as an ultrasound image and overlaying, on the ultrasound image at the user interface, the real-time guidance data, wherein the real-time guidance data includes visual feedback configured to direct a user in real-time to adjust a catheter's position. In an embodiment the real-time guidance data as a function of one or more changes in the ultrasound data and probe position data. In an embodiment, step 925 may further include updating the real-time guidance data including a set of visual indicators as a function of one or more movements of a catheter, wherein the set of visual indicators show a relative proximity of the catheter to a target area. This may be implemented, without limitation, as referenced in FIGS. 1-8.

Still referring to FIG. 9, method 900 may include a step 930 of displaying the real-time guidance data to a user through a user interface. This may be implemented, without limitation, as referenced in FIGS. 1-8.

In continued reference to FIG. 9, in an embodiment, method 900 may include a step of displaying, at a display device, visual feedback to a user as a function of the real-time guidance, wherein the visual feedback includes an on-screen visual guide. This may be implemented, without limitation, as referenced in FIGS. 1-8.

With further reference to FIG. 1, in an embodiment, method 900 may include a step of receiving a 3D model of a target region, wherein the 3D model is generated using CT data, training a scoring-based canonical view simulation model, wherein training includes using a plurality of ultrasound and CT data pairs to simulate a capturing of canonical views by guiding an ultrasound device that is simulated from a virtual sensor positioning within the CT data, and displaying, at the user interface, a position of the virtual sensor relative to the 3D model as a function of the probe position data. This may be implemented, without limitation, as referenced in FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
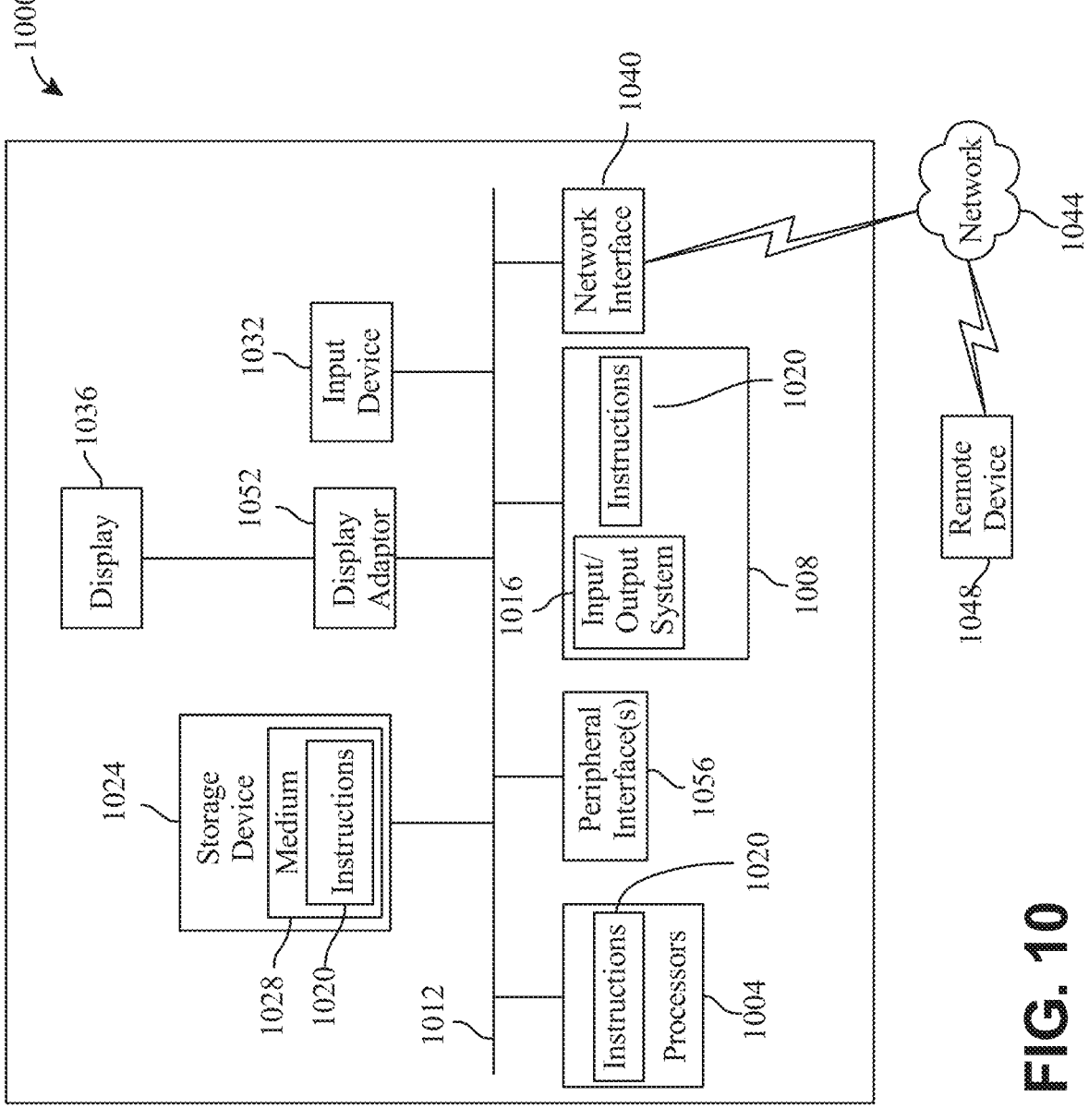
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIRE-WIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for guiding ultrasonic probe positioning using a scoring-based canonical view simulation model, the system comprising:
    a catheter coupled to at least a transducer, wherein the at least a transducer is configured to receive ultrasound data;
    a localization system configured to detect probe position data as a function of a location of the catheter;
    at least a processor communicatively connected to the at least a transducer and the localization system; and
    a memory communicatively connected to the at least a processor, wherein the memory contains instructions configuring the at least a processor to:
    receive the ultrasound data from the transducer;
    receive the probe position data from the localization system;
    generate, using a scoring-based canonical view simulation model, a movement vector as a function of the ultrasound data and the probe position data, wherein the scoring-based canonical view simulation model has been trained using a reinforcement learning algorithm;
    determine, using the movement vector, real-time guidance data comprising a performance metric, wherein the performance metric is determined as a function of comparing actions of a user, as represented by one or both of the ultrasound data and the probe position data, against an optimal movement predicted by the scoring-based canonical view simulation model; and
    display the real-time guidance data and the performance metric in real-time to the user through a user interface.

2. The system of claim 1, wherein:
    the real-time guidance data comprises an optimal movement of the catheter which is a function of the movement vector; and
    the real-time guidance data comprises one or more of visual feedback, auditory feedback, or haptic feedback.

3. The system of claim 1, further comprising a display device, wherein:
    the real-time guidance data comprises visual feedback, wherein visual feedback comprises an on-screen visual guide; and
    the display device is configured to display the visual feedback to a user as a function of the real-time guidance data.

4. The system of claim 1, wherein the at least a processor is further configured to:
    display, through the user interface, the ultrasound data as an ultrasound image; and overlay, on the ultrasound image at the user interface, the real-time guidance, wherein the real-time guidance data comprises visual feedback configured to direct a user in real-time to adjust the catheter's position.

5. The system of claim 1, wherein the at least a processor is further configured to:
    display, through the user interface, a 3D model; and
    overlay, on the 3D model at the user interface, the position of a virtual sensor relative to the 3D model as a function of the probe position data.

6. The system of claim 1, wherein the at least a processor is further configured to update the real-time guidance data as a function of one or more changes in the ultrasound data and probe position data, wherein updating the real-time guidance data comprises:
    receiving updated ultrasound data and probe position data;
    inputting the updated ultrasound and probe position data into the scoring-based canonical view simulation model; and
    outputting, from the scoring-based canonical view simulation model, updated real-time guidance.

7. The system of claim 1, wherein the scoring-based canonical view simulation model comprises a reinforcement learning model that has been trained using computed tomography data.

8. The system of claim 1, wherein:
    the real-time guidance data comprises a set of visual indicators, wherein the set of visual indicators show a relative proximity of the catheter to a target area; and
    the at least a processor is further configured to update the set of visual indicators as a function of one or more movements of the catheter.

9. The system of claim 1, wherein:
    the ultrasound data and the probe position data are live data; and
    the ultrasound data and the probe position data are received from a live ultrasonic procedure.

10. A method for guiding ultrasonic probe positioning using a scoring-based canonical view simulation model, the method comprising:
    receiving, by at least a processor, ultrasound data from a transducer coupled to a catheter;
    receiving, by the at least a processor, probe position data from a localization system;
    generating, using a scoring-based canonical view simulation model, a movement vector as a function of the ultrasound data and the probe position data, wherein the scoring-based canonical view simulation model has been trained using a reinforcement learning algorithm;
    determining, using the movement vector, real-time guidance data comprising a performance metric, wherein the performance metric is determined as a function of comparing actions of a user, as represented by one or both of the ultrasound data and the probe position data, against an optimal movement predicted by the scoring-baser canonical view simulation model; and
    displaying the real-time guidance data and the performance metric in real-time to the user through a user interface.

11. The method of claim 10, wherein:
    the real-time guidance data comprises an optimal movement of the catheter which is a function of the movement vector; and
    the real-time guidance data comprises one or more of visual feedback, auditory feedback, or haptic feedback.

12. The method of claim 10, further comprising displaying, to a user, real-time guidance comprising visual feedback, wherein the visual feedback comprises an on-screen visual guide.

13. The method of claim 10, further comprising:

displaying, through the user interface, the ultrasound data as an ultrasound image; and overlaying, on the ultrasound image at the user interface, the real-time guidance, wherein the real-time guidance data comprises visual feedback configured to direct a user in real-time to adjust the catheter's position.

14. The method of claim 10, further comprising:

displaying, through the user interface, a 3D model; and overlaying, on the 3D model at the user interface, the position of a virtual sensor relative to the 3D model as a function of the probe position data.

15. The method of claim 10, further comprising updating the real-time guidance data as a function of one or more changes in the ultrasound data and probe position data, wherein updating the real-time guidance data comprises:

receiving updated ultrasound data and probe position data;

inputting the updated ultrasound and probe position data into the scoring-based canonical view simulation model; and outputting, from the scoring-based canonical view simulation model, updated real-time guidance.

16. The method of claim 10, wherein the scoring-based canonical view simulation model comprises a reinforcement learning model that has been trained using computed tomography data.

17. The method of claim 10, further comprising updating the real-time guidance data comprising a set of visual indicators as a function of one or more movements of the catheter, wherein the set of visual indicators show a relative proximity of the catheter to a target area.

18. The method of claim 10, wherein:

the ultrasound data and the probe position data are live data; and the ultrasound data and the probe position data are received from a live ultrasonic procedure.

* * * * *